United States Patent [19]

Rimbault

[11] Patent Number: 4,797,414
[45] Date of Patent: Jan. 10, 1989

[54] NAPHTHOTHIOPHENE DERIVATIVES AND THEIR USE AS RESPIRATORY ENHANCING AGENTS

[75] Inventor: Christian G. Rimbault, Grand-Lancy, Switzerland

[73] Assignee: Zyma SA, Nyon, Switzerland

[21] Appl. No.: 829,631

[22] Filed: Feb. 14, 1986

[30] Foreign Application Priority Data

Feb. 23, 1985 [GB] United Kingdom ............... 8504702

[51] Int. Cl.$^4$ ............... A61K 31/38; C07D 333/74
[52] U.S. Cl. ............................. 514/443; 514/253; 514/228.2; 514/233.5; 514/233.8; 549/43; 549/44; 549/45; 549/46; 549/47; 549/26; 549/24; 549/42; 544/60; 544/126; 544/361; 548/237; 548/253
[58] Field of Search .............. 549/43, 44, 45, 46, 549/47, 26, 24; 544/60, 126, 361; 514/225, 231, 253, 443

[56] References Cited

U.S. PATENT DOCUMENTS 3,656,906 4/1972 Bullock ........................ 549/43

FOREIGN PATENT DOCUMENTS 042536 12/1981 European Pat. Off. .......... 549/43
1917601 10/1970 Fed. Rep. of Germany ...... 549/43
1953809 4/1971 Fed. Rep. of Germany ...... 549/43
2803984 8/1978 Fed. Rep. of Germany ...... 549/43

OTHER PUBLICATIONS

Indian J. Chem., vol. 20B, Mar. 1981, p. 243.
Liebigs Ann. Chem. (1981), p. 347.
J. Chem. Soc. Perkin Tr. I (1977), p. 63.
C. A. 84: 74018t, (1976), Application of the method for thiophene heterocycle synthesis using sodium sulfide to the preparation of sulfur analogs of polycyclic aromatic hydrocarbons.
J. Prakt. Chem., 314: p. 499 (1972).
C. A. 72: 111328u, (1970), New heterocyclic systems, III, Heterocycles containing a fused thiophene ring.
C. A. 78: 147716g (1973), Condensation of (β-chlorovinyl)carbonyl compounds with a α-mercaptocaraaboxylic acids.
J. Chem Soc. Perkin I (1973), p. 2956.
Tetrahedron Letters No. 11 (1968), pp. 1317-1319.

Primary Examiner—Mary C. Lee
Assistant Examiner—J. Richter
Attorney, Agent, or Firm—Irving M. Fishman; JoAnn Villamizar

[57] ABSTRACT

Pharmaceutical preparations containing compounds of formula I

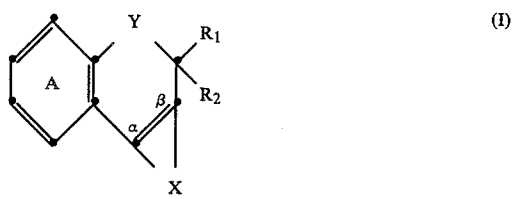

wherein ring A is unsubstituted or substituted, $R_1$ and $R_2$, independently of one another, each represents hydrogen, lower alkyl, aryl or heteroaryl, or $R_1$ and $R_2$ together represent lower alkylene optionally interrupted by oxygen, sulfur or optionally substituted nitrogen, Y is methylene, methylene mono- or disubstituted by lower alkyl, oxygen, sulfur, sulfinyl or sulfonyl, X represents a bivalent radical $-S-C[-B-(Z)_n]=CH-$ the sulfur group S of which is bonded directly to the $\alpha$- or to the $\beta$-position of the bicyclic ring system, B denotes a direct bond, alkylene or alkenylene; n is 1 or, in case B is alkylene or alkenylene, may be also 2 or 3; and Z represents free or functionally modified carboxy, masked carboxy that can be cleaved under physiological conditions, free or functionally modified formyl, acyl, free or functionally modified sulfo, free, etherified or esterified hydroxy, free, etherified or oxidised etherified mercapto, unsubstituted or substituted amino, ammonio, nitro or halogen; and novel compounds of formula I are disclosed. The latter are prepared by methods known per se.

22 Claims, No Drawings

NAPHTHOTHIOPHENE DERIVATIVES AND THEIR USE AS RESPIRATORY ENHANCING AGENTS

The invention relates to pharmaceutical preparations containing 1,2-dihydronaphthalenes and 1-oxa, 1-thia, 1-sulfinyl and 1-sulfonyl derivatives thereof, the therapeutic use of these compounds, novel compounds of this kind and processes for their manufacture. These compounds have valuable pharmaceutical properties.

The invention relates in particular to pharmaceutical preparations containing compounds of formula I

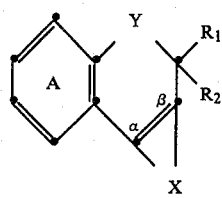

wherein ring A is unsubstituted or substituted, $R_1$ and $R_2$, independently of one another, each represents hydrogen, lower alkyl, aryl or heteroaryl, or $R_1$ and $R_2$ together represent lower alkylene optionally interrupted by oxygen, sulfur or optionally substituted nitrogen, Y is methylene, methylene mono- or disubstituted by lower alkyl, oxygen, sulfur, sulfinyl or sulfonyl, X represents a bivalent radical —S—C[—B—(Z)$_n$]═CH— the sulfur group S of which is bonded directly to the α- or to the β-position of the bicyclic ring system, B denotes a direct bond, alkylene or alkenylene; n is 1 or, in case B is alkylene or alkenylene, may be also 2 or 3; and Z represents free or functionally modified carboxy, masked carboxy that can be cleaved under physiological conditions, free or functionally modified formyl, acyl, free or functionally modified sulfo, free, etherified or esterified hydroxy, free, etherified or oxidised etherified mercapto, unsubstituted or substituted amino, ammonio, nitro or halogen; or tautomers, stereoisomers or optical isomers thereof, or mixtures of these optical isomers; or pharmaceutically acceptable salts thereof.

The numbering of substituents within the compounds of formula I, in accordance with IUPAC nomenclature regulations, is as follows:

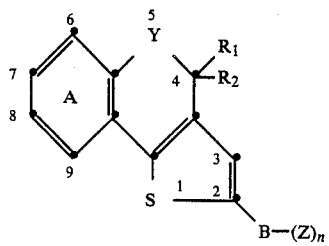

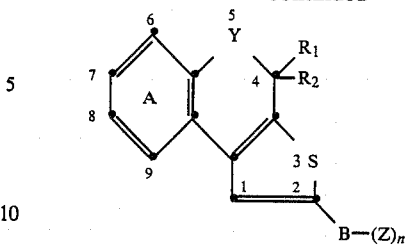

In case Y is sulfinyl the corresponding sulfoxide compound may exist in its α- or its β-form. The same is valid for any sulfoxide-type substituent(s) present in the molecule, e.g. a lower alkylsulfinyl group.

The term "lower" means that groups so defined have for example up to and including 7, preferably up to and including 4, carbon atoms.

Substituted radicals may contain one or more identical or different substituents; these may substitute any suitable position. Preferably substituted radicals are mono- or disubstituted, and in particular they are monosubstituted.

The ring A is unsubstituted or substituted by 1, 2, 3 or 4 substituents, preferably by 1 or 2 and in particular by 1 substituent. Substituents are, inter alia, optionally substituted hydrocarbon radicals, such as corresponding aliphatic, cycloaliphatic, aromatic or araliphatic hydrocarbon radicals, such as lower alkyl, lower alkenyl, lower alkynyl, lower alkylene linked to ring A in two adjacent positions and forming a 5-, 6- or 7-membered ring, cycloalkyl and/or phenyl-lower alkyl; substituents of such hydrocarbon radicals, especially of lower alkyl, cycloalkyl and/or phenyl-lower alkyl, may be, for example, optionally etherified or esterified hydroxy groups, such as hydroxy, lower alkoxy, halo-lower alkoxy, lower alkenyloxy, lower alkynyloxy, lower alkylenedioxy or lower alkanoyloxy, halogen, and/or optionally functionally modified carboxy, such as carboxy, esterified carboxy, for example lower alkoxycarbonyl, amidated carboxy, such as carbamoyl, lower alkylcarbamoyl or di-lower alkylcarbamoyl, or cyano. In addition, cyclic substituents, especially phenyl, may contain as substituent also lower alkyl which may be optionally substituted, for example as indicated. Further substituents are, for example, optionally etherified or esterified hydroxy groups, such as hydroxy, lower alkoxy, halo-lower alkoxy, lower alkenyloxy, halo-lower alkenyloxy, lower alkynyloxy, lower alkylenedioxy or lower alkanoyloxy, halogen, nitro, optionally substituted amino, such as amino, lower alkylamino, di-lower alkylamino, N-lower alkyl-N-phenyl-lower alkylamino, lower alkyleneamino, oxa-, thia-, or aza-lower alkyleneamino, it being possible for the aza-nitrogen atom to be unsubstituted or substituted, preferably by lower alkyl, but also e.g. by phenyl or phenyl-lower alkyl which substituents themselves are optionally substituted, for example as described above, or by acyl, e.g. lower alkanoyl or benzoyl; or acylamino, for example lower alkanoylamino, formyl, acyl, such as lower alkanoyl, or optionally functionally modified carboxy, such as carboxy, esterified carboxy, for example lower alkoxycarbonyl, or amidated carboxy, such as carbamoyl, lower alkylcarbamoyl or di-lower alkylcarbamoyl, or cyano, optionally functionally modified sulfo, such as sulfo, sulfamoyl, lower alkyl-, di-lower alkyl or phenylsulfamoyl, and/or etherified mercapto, which may optionally be oxidised, such as lower alkylthio, lower alkylsulfinyl or lower alkylsulfonyl. Preferred as substituents of the ring A are lower alkyl, hydroxy, lower alkoxy and halogen.

Lower alkyl is, for example, n-propyl, isopropyl, n-butyl, isobutyl, sec.-butyl or tert.-butyl, also n-pentyl, isopentyl, neopentyl, n-hexyl, isohexyl or n-heptyl, but preferably ethyl and especially methyl.

An aryl or heteroaryl radical is especially a corresponding monocyclic radical but may also be a bicyclic or polycyclic carbocyclic or heterocyclic radical having aromatic properties. Aryl is especially phenyl, also naphthyl, for example 1- or 2-naphthyl.

Heteroaryl is preferably monocyclic but may also be bicyclic or polycyclic. In the latter cases it may consist of several aromatic heterocyclic rings, or of one or more aromatic heterocyclic rings having one or more fused-on aromatic carbocyclic rings, especially one or more fused-on benzo rings. The heteroaryl radicals which are normally present and which preferably consist of five or six ring members, may contain as ring members up to four identical or different hetero atoms, especially nitrogen, oxygen and/or sulfur atoms, preferably one, two, three or four nitrogen atoms, one oxygen or sulfur atom, or one or two nitrogen atoms together with one oxygen atom or one sulfur atom.

Monocyclic five-membered heteroaryl radicals are, for example, corresponding monoaza-, diaza-, triazatetraza-, monooxa-, monothia-, oxaza-, oxadiaza-, thiaza- or thiadiaza-cyclic radicals, such as pyrryl, pyrazolyl, imidazolyl, triazolyl, tetrazolyl, furyl, thienyl, isoxazolyl, oxazolyl, oxadiazolyl, isothiazolyl, thiazolyl or thiadiazolyl radicals, while monocyclic, six-membered heteroaryl radicals are, for example, corresponding monoaza-, diaza- or triaza-cyclic radicals, such as pyridyl, pyridazinyl, pyrimidinyl, pyrazinyl or triazinyl radicals. Bicyclic heteroaryl radicals are especially monocyclic heteroaryl radicals having a fused-on benzo ring; the hetero ring may be five- or six-membered, the five-membered heteroaryl radical being, for example, a monoaza-, diazamonooxa-, monothia-, oxaza- or thiazacyclic radical, and the six-membered heteroaryl radical being, for example, a monoaza- or a diaza-cyclic heteroaryl radical. Such bicyclic radicals are, for example, indolyl, isoindolyl, benzimidazolyl, benzofuranyl, benzothienyl, benzoxazolyl, benzothiazolyl, quinolinyl or isoquinolinyl radicals.

Heteroaryl, in the first instance, is pyrryl, pyrazolyl, imidazolyl, furyl, thienyl, pyridyl, pyrimidinyl or quinolyl.

Aryl and heteroaryl radicals may be unsubstituted or substituted, it being possible especially for ring carbon atoms, but also for ring nitrogen atoms, to be substituted. Substituents of ring carbon atoms are e.g. those indicated above for the ring A. Substituents of ring nitrogen atoms are e.g. free or functionally modified carboxy, such as lower alkoxycarbonyl, an aliphatic hydrocarbon radical, such as lower alkyl, lower alkanoyl or benzoyl, also hydroxy, lower alkoxy or lower alkanoyloxy.

Heteroaryl may be in various tautomeric forms, depending on the nature of the substituents.

Lower alkylene optionally interrupted by an oxygen, sulfur or nitrogen atom, formed by the radicals $R_1$ and $R_2$ together, is preferably lower alkylene having from 2 to 6, especially 4 or 5 chain carbon atoms, or oxa-, thia- or aza-lower alkylene each having from 3 to 5, especially 3 or 4 chain carbon atoms besides the corresponding hetero atom. In particular it is 1,5-pentylene. Within an aza-lower alkylene radical, the aza-nitrogen may be substituted by e.g. an aliphatic hydrocarbon radical, such as lower alkyl, or by acyl, such as lower alkanoyl or benzoyl.

Alkylene represents e.g. $(C_1-C_{12})$alkylene, such as decylene, and is preferably lower alkylene. Lower alkylene is e.g. propylene, such as 1,3-, 1,2- or 1,1-propylene, butylene, pentylene, hexylene or heptylene, preferably $(C_1-C_4)$alkylene, especially ethylene and in particular methylene.

Alkenylene represents e.g. $(C_2-C_{12})$alkenylene, such as decenylene, and is preferably lower alkenylene. Lower alkenylene is e.g. 1- or 2-propenylene, such as 1,3-prop-1-enylene or 1,2-prop-1-enylene, 1-, 2- or 3-butenylene, 1-, 2- or 4-pentenylene, 1-, 2-, 3- or 5-hexenylene, or 1-, 2, 3-, 4- or 6-heptenylene, preferably $(C_2-C_4)$alkenylene and especially ethenylene, such as 1,2-ethenylene.

Free or functionally modified carboxy is, for example, carboxy, esterified carboxy, preferably alkoxycarbonyl the alkoxy portion of which contains e.g. 1 to 16, preferably 1 to 10 and especially 1 to 8 carbon atoms, such as octoxycarbonyl, in particular lower alkoxycarbonyl, such as methoxycarbonyl or ethoxycarbonyl, but also phenyloxycarbonyl or heterocyclyloxycarbonyl; amidated carboxy, e.g. carbamoyl which is optionally substituted by one or two equal or different radicals selected from the group comprising lower alkyl, phenyl-lower alkyl, (halo, lower alkyl, hydroxy, lower alkoxy, nitro)-phenyl-lower alkyl, phenyl, heterocyclyl, amino, lower alkylamino, di-lower alkylamino, phenylamino and di-phenylamino, preferably carbamoyl, lower alkylcarbamoyl [—CONH(lower alkyl)], phenyl-lower alkylcarbamoyl, halo-phenyl-lower alkylcarbamoyl, di-lower alkylcarbamoyl [—CON(lower alkyl)$_2$] or aminocarbamoyl (—CONHNH$_2$); hydroxycarbamoyl (—CONHOH); or cyano.

Further comprised are heterocyclic derivatives of carboxy, preferably 5-tetrazolyl, unsubstituted or lower alkylsubstituted 4,5-dihydro-2-oxazolyl, or 4,5-dihydro-2-thiazolyl which is optionally substituted in 4-position by free or functionally modified carboxy, especially carboxy, but also e.g. unsubstituted, lower alkyl- or phenyl-substituted 5,6-dihydro-4H-1,3-oxazin-2-yl.

Masked carboxy that can be cleaved under physiological conditions represents any carboxy derivative that is convertible under physiological conditions to carboxy, especially prodrug esters but also e.g. prodrug amides thereof.

Said prodrug esters are preferably acyloxymethoxycarbonyl, such as lower alkanoyloxy-methoxycarbonyl, e.g. pivaloyloxy-methoxycarbonyl or acetoxymethoxycarbonyl; amino-lower alkanoyloxy-methoxycarbonyl, especially α-amino-lower alkanoyloxy-methoxycarbonyl, e.g. glycyl-, L-valyl- or L-leucyloxy-methoxycarbonyl; lower alkanoylamino-methoxycarbonyl; 3-phthalidyloxycarbonyl; 1-lower alkoxycarbonyloxy-lower alkoxycarbonyl, such as 1-ethoxycarbonyloxy-ethoxycarbonyl; 1-lower alkoxy-lower alkoxycarbonyl, such as methoxy-methoxycarbonyl or 1-methoxy-ethoxycarbonyl; or 2-oxo-1,3-dioxolen-4-ylmethoxycarbonyl that optionally is substituted by lower alkyl or phenyl in 5-position of the dioxolene ring.

Said prodrug amides are e.g. monosubstituted carbamoyl groups derived from the amino acids or functionally modified derivatives, e.g. lower alkyl esters, thereof, e.g. from glycine, alanine, phenylalanine and the like, such as carboxymethyl-carbamoyl.

Free or functionally modified formyl is preferably formyl or imino (—CH=NH) which may be substituted by free, etherified or esterified hydroxy, such as hydroxy, lower alkoxy, lower alkanoyloxy or benzoyloxy, by lower alkyl, phenyl or amino (it being optionally possible for amino to contain as substituent(s) 1 or 2 lower alkyl groups, 1 or 2 phenyl groups or carbamoyl which is optionally mono- or disubstituted by lower alkyl); but may be also an acetal such as a di-lower alkylacetal. Further comprised are heterocyclic derivatives of formyl, especially 2-thiazolidinyl which is optionally substituted in 4-position by free or functionally modified carboxy, especially carboxy.

Acyl is the corresponding radical of a carboxylic acid, preferably benzoyl, especially lower alkanoyl or halo-lower alkanoyl, and also phenyl-lower alkanoyl, heterocyclylcarbonyl or heterocyclyl-lower alkanoyl.

Free or functionally modified sulfo is, for example, sulfo (13 SO$_3$H), esterified sulfo, such as lower alkoxysulfonyl, phenyloxysulfonyl or heterocyclyloxysulfonyl; amidated sulfo, such as sulfamoyl which is optionally substituted by one or two equal or different radicals selected from the group comprising lower alkyl, phenyl and heterocyclyl, preferably sulfamoyl, lower alkylsulfamoyl or di-lower alkylsulfamoyl; or sulfonyl halide, such as sulfonyl chloride.

Etherified hydroxy is e.g. hydroxy etherified by a hydrocarbon radical, especially lower alkoxy, also, for example, lower alkenyloxy, lower alkynyloxy, phenyloxy, phenyl-lower alkoxy, heterocyclyloxy or heterocyclyl-lower alkoxy.

Esterified hydroxy is e.g. hydroxy esterified by a carboxylic acid, such as acyloxy, preferably alkanoyloxy which contains e.g. 1 to 20, preferably 1 to 16, carbon atoms, especially lower alkanoyloxy, or benzoyloxy, but may be also e.g. lower alkoxycarbonyloxy.

Etherified mercapto is e.g. mercapto etherified by a hydrocarbon radical, in particular lower alkylthio, preferably unsubstituted or substituted by free or esterified carboxy, such as carboxy-methylthio or lower alkoxycarbonyl-methylthio, also phenylthio or phenyl-lower alkylthio, heterocyclylthio or heterocyclyl-lower alkylthio.

Oxidised etherified mercapto is e.g. a sulfoxide or a sulfone of the etherified mercapto groups as defined above, preferably phenylsulfinyl, phenyl-lower alkylsulfinyl, lower alkylsulfinyl, phenylsulfonyl or phenyl-lower alkylsulfonyl, and especially lower alkylsulfonyl.

An unsubstituted or substituted amino group can be a primary, secondary or tertiary amino group. In the two last-mentioned amino groups, the nitrogen atom may contain as substituent(s) e.g. unsubstituted or substituted aliphatic, cycloaliphatic, cycloaliphatic-aliphatic, aromatic, araliphatic, heterocyclic or heterocyclic-aliphatic hydrocarbon radicals, or acyl. Two substituents taken together may also be an bivalent aliphatic hydrocarbon radical, for example lower alkylene in which 1 (or 2) chain carbon atom(s) are optionally replaced by 1 or 2, preferably 1, heteroatom(s) selected from the group comprising e.g. oxygen, sulfur or optionally substituted nitrogen.

Secondary amino is in particular lower alkylamino, also cycloalkylamino, phenylamino, phenyl-lower alkylamino, heterocyclylamino, heterocyclyl-lower alkylamino, acylamino, especially lower alkanoylamino or halo-lower alkanoylamino, e.g. trifluoroacetylamino, but also e.g. benzoylamino or phenyl-lower alkanoylamino, or hydrazino which is optionally mono-, di- or tri-substituted by hydrocarbon radicals, such as phenyl and/or lower alkyl.

Tertiary amino is in particular di-lower alkylamino, also N-cycloalkyl-N-lower-alkylamino, e.g. N-cyclopentyl-N-methylamino, N-phenyl-N-lower-alkylamino, e.g. N-methyl-N-phenylamino, or N-lower-alkyl-N-phenyl-lower-alkylamino, e.g. N-benzyl-N-methylamino, lower alkyleneamino, oxa- , thia- or aza-lower alkyleneamino (in the latter of which the aza-nitrogen atom may be substituted e.g. by a hydrocarbon radical, such as lower alkyl, phenyl or phenyl-lower alkyl, or by acyl, such as lower alkanoyl), or di-acylamino, such as di-lower alkanoylamino or di-benzoylamino.

Ammonio comprises e.g. quaternary ammonium salts derived from corresponding tertiary amino groups mentioned above, which contain as quaternary substituent e.g. optionally substituted lower alkyl, preferably lower alkyl, hydroxy- or halo-lower alkyl, phenyl-lower alkyl, phenoxy-lower alkyl or phenylthio-lower alkyl, wherein the phenyl moiety in each case is optionally substituted by e.g. lower alkyl, lower alkoxy, halogen, trifluoromethyl and/or by nitro. Especially ammonio is tri-lower alkylammonio such as trimethylammonio, but also e.g. phenyl-lower-alkyl-di-lower-alkylammonio or phenoxy-lower-alkyl-di-lower-alkylammonio. They correspond to the salts defined hereinafter, especially the salts mentioned in particular as being pharmaceutically acceptable, non-toxic acid addition salts, and more especially to those salts formed with hydrohalic acids, sulfuric or phosphoric acid.

Within the radical Z, alkyl and lower alkyl groups [including all radicals containing one or more alkyl or lower alkyl portions, for example alkoxycarbonyl, alkanoyloxy, lower alkoxy, lower alkylthio, lower alkylamino, lower alkanoyl(oxy) and the like] and especially phenyl and heterocyclyl groups (including all radicals containing one or more phenyl and/or heterocyclyl portions, for example phenyloxy, heterocyclyloxy, phenylamino, heterocyclylamino, benzoyl, heterocyclylcarbonyl and the like), independently of one another, are optionally substituted by hydroxy, lower alkoxy, lower alkanoyloxy, halogen, mercapto, lower alkylthio, carboxy, lower alkoxycarbonyl, carbamoyl, lower alkylcarbamoyl, di-lower alkylcarbamoyl, cyano, nitro, amino, lower alkylamino, di-lower alkylamino, lower alkanoylamino, benzoylamino, di-lower alkanoylamino, di-benzoylamino, lower alkyleneamino, oxa-, thia- and/or aza-lower alkyleneamino, and phenyl groups as well as heterocyclyl groups furthermore may be substituted by lower alkyl, formyl, sulfo, sulfamoyl, lower alkyl-, di-lower alkyl- and/or phenylsulfamoyl.

The preferred substituents of alkyl and lower alkyl groups and especially phenyl and heterocyclyl groups occurring within the radical Z are hydroxy, lower alkoxy, lower alkanoyloxy, halogen, lower alkylthio, carboxy, lower alkoxycarbonyl, carbamoyl, cyano, nitro, lower alkylamino, di-lower alkylamino, lower alkanoylamino, and/or lower alkyleneamino, and for phenyl and heterocyclyl also lower alkyl, formyl, sulfo and/or sulfamoyl.

Halogen, as a meaning of Z, is preferably bromo, especially chloro, but also iodo or fluoro.

Halogen, in general, is e.g. bromo or iodo, preferably fluoro and especially chloro.

Lower alkenyl is, for example, allyl or methallyl, and lower alkynyl is, for example, propargyl.

Cycloalyl contains preferably from 3 to 8, especially 5 or 6, ring members and is, for example, cyclopentyl or cyclohexyl, and also cyclopropyl and cycloheptyl.

Phenyl-lower alkyl is, for example, benzyl or 1- or 2-phenylethyl.

Lower alkoxy is preferably methoxy, also ethoxy, n-propoxy, isopropoxy, n-butoxy, isobutoxy or tert.-butoxy, and also n-pentyloxy, n-hexyloxy or n-heptyloxy.

Halo-lower alkoxy may contain one or more halogen atoms, preferably fluoro and/or chloro. It represents e.g. 1,1,2-trifluoro-2-chloroethoxy or, preferably, difluoromethoxy.

Phenyl-lower alkoxy is e.g. benzyloxy.

Lower alkenyloxy is, for example, allyloxy or methallyloxy, and halo-lower alkenyloxy, which may contain one or more halogen atoms, preferably fluorine and/or chlorine, is for example 1,2-dichlorovinyloxy.

Lower alkynyloxy is, for example, propargyloxy while lower alkylenedioxy is, for example, methylenedioxy or ethylenedioxy.

Alkanoyloxy is e.g. ($C_1$-$C_{20}$)alkanoyloxy, such as palmitoyloxy, or preferably lower alkanoyloxy, such as acetoxy, propionyloxy or pivaloyloxy, and also formyloxy.

Lower alkylcarbamoyl is, for example, methylcarbamoyl or ethylcarbamoyl, while di-lower alkylcarbamoyl is, for example, dimethylcarbamoyl or diethylcarbamoyl.

Lower alkylamino is, for example, methylamino, ethylamino, n-propylamino or isopropylamino.

Di-lower alkylamino is, for example, dimethylamino, ethylmethylamino or diethylamino. Cycloalkylamino is e.g. cyclohexylamino, while phenyl-lower alkylamino is e.g. benzylamino.

Lower alkyleneamino contains, for example, from 2 to 7, preferably 4 to 6, ring carbon atoms and is, for example, pyrrolidino or piperidino, while oxa-lower alkyleneamino is e.g. 4-morpholino, thia-lower alkyleneamino represents e.g. 4-thiomorpholino, and optionally aza-substituted aza-lower alkyleneamino is, for example, 1-piperazino, 4-methyl-1-piperazino, 4-phenyl-1-piperazino, 4-benzyl-1-piperazino or 4-(2-phenylethyl)-1-piperazino.

Lower alkanoyl is e.g. acetyl, propionyl or pivaloyl. Halo-lower alkanoyl is preferably trifluoroacetyl. Phenyl-lower alkanoyl is e.g. phenylacetyl. Lower alkanoylamino is preferably acetylamino or propionylamino, but also formylamino. Phenyl-lower alkanoylamino is e.g. phenylacetylamino.

Lower alkylsulfamoyl is e.g. methyl- or ethylsulfamoyl, while di-lower alkylsulfamoyl is e.g. dimethyl- or diethylsulfamoyl.

Lower alkylthio is, for example, methylthio, ethylthio, n-propylthio or isopropylthio, while lower alkylsulfinyl is, for example, methylsulfinyl, and lower alkylsulfonyl is, for example, methylsulfonyl or ethylsulfonyl. Phenyl-lower alkylthio is e.g. benzylthio or 2-phenylethylthio, while phenyl-lower alkylsulfinyl is, for example, benzylsufinyl or 2-phenylethylsulfinyl, and phenyl-lower alkylsulfonyl represents e.g. benzylsulfonyl or 2-phenylethylsulfonyl.

Lower alkoxycarbonyloxy is, for example, methoxycarbonyloxy or ethoxycarbonyloxy.

Heterocyclyl, as such or within radicals containing a heterocyclyl portion, e.g. heterocyclyloxycarbonyl, heterocyclylcarbonyl, heterocyclyl-lower alkanoyl, heterocyclyloxysulfonyl, heterocyclyloxy, heterocyclyl-lower alkoxy, heterocyclylthio, heterocyclyl-lower alkylthio, heterocyclylamino or heterocyclyl-lower alkylamino, represents preferably heteroaryl as defined above, but also the heteroaryl radicals as defined above when partially or completely saturated provided in the latter case that the radicals are bonded by a carbon atom.

Salts of compounds of the formula I are especially pharmaceutically acceptable non-toxic salts, such as those of compounds of the formula I with acidic groups, for example with a free carboxy or sulfo group. Such salts are especially metal or ammonium salts, such as alkali metal or alkaline earth metal salts, for example sodium, potassium, magnesium or calcium salts, as well as ammonium salts, which are formed with ammonia or suitable organic amines. There come into consideration for the salt formation especially aliphatic, cycloaliphatic, cycloaliphatic-aliphatic or araliphatic primary, secondary or tertiary mono-, di- or poly-amines, as well as heterocyclic bases, such as lower alkylamines, for example di- or tri-ethylamine, hydroxy-lower alkylamines, such as 2-hydroxyethylamine, bis-(2-hydroxyethyl)-amine or tris-(2-hydroxyethyl)-amine, basic aliphatic esters or carboxylic acids, e.g. 4-aminobenzoic acid 2-diethylaminoethyl ester, lower alkyleneamines, e.g. 1-ethylpiperidine, cycloalkylamines, e.g. dicyclohexylamine, benzylamines, e.g. N,N'-dibenzylethylenediamine, or bases of the pyridine typ, e.g. pyridine, collidine or quinoline.

Compounds of the formula I having a basic group may form acid addition salts, for example with inorganic acids, such as hydrochloric acid, sulfuric acid or phosphoric acid, with suitable organic carboxylic or sulfonic acids, e.g. acetic acid, trifluoroacetic acid, succinic acid, fumaric acid, tartaric acid, methanesulfonic acid or p-toluenesulfonic acid, or with amino acids, such as arginine or lysine. In the presence of several acidic or basic groups, mono- or poly-salts may be formed. Compounds of the formula I having an acidic group, for example a free carboxy group, and a basic group, for example an amino group, may also be present in the form of inner salts, i.e. in zwitterionic form, or a part of the molecule may be present in the form of an inner salt and another part in the form of a normal salt.

The pharmaceutically acceptable salts mentioned hereinbefore are preferred. For isolation or purification it is also possible to use other salts than the therapeutically acceptable salts, for example the picrates.

The compounds of formula I possess valuable pharmacological properties. They, for example, stimulate the mucociliary transport in bronchia, and they modify the secretion or the viscoelasticity of mucus produced by bronchial and tracheal glands. These properties make the compounds useful for the treatment of diseases of the respiratory tract, as for example chronic bronchitis, in mammals including men.

The stimulation of mucociliary transport can be demonstrated with pharmacological model of frog oesophagus. In this system, the speed of transport of particles by the ciliated epithelium of frog oesophagus is measured according to Puchelle et al. [Bull. Physio. path. resp. 12, 771–779 (1976)].

By adding solutions of compounds to be tested on the frog oesophagus an increase in the speed of transport is measured. This effect appears when using solutions of compounds of formula I with a concentration of only $10^{-3}$–$10^{-4}$M or less.

The relaxing effect of these compounds on the smooth muscles of bronchi can be demonstrated by the protection afforded by these compounds against the broncho-spasm induced by histamine aerosol in Guinea-pigs. Pretreatment of Guinea-pigs by i.p. route with compounds of formula I at a dose of 100 mg/kg or less allows the animals to resist more than 5 minutes to the histamine aerosol; control animals do not resist more than 1 minute and 30 sec.

The modification of viscoelasticity of mucus samples caused by compounds of formula I can be measured with a microrheometer according to C. Marriott [Advances in experimental Medicine and Biology 144, 75–84 (1981)].

The mucus is obtained from fresh pig's stomach scrapings and is purified biochemically before use. The test compounds are dissolved in specific solvents, distilled water, phosphate buffer, methanol aqueous mixture, or in DMSO (dimethylsulfoxide). 50 mg aliquotes of mucus with 5–10 μl of the test solution are added. The samples are mixed, centrifuged and incubated for 30 min. for interaction to take place. The samples are then loaded into the cell of an oscillating sphere magnetic microrheometer and a 200 μm iron sphere is placed centerally in the sample which is allowed 5 minutes for relaxation to take place. The rheological behaviour is evaluated at 25° C. over the frequency range of 0.1 to 20 Hz. The elastic modulus G' of mucus is changed, preferably reduced, but also enlarged, by using the compounds of formula I.

The mucoregulators properties of the compounds of formula I can be evaluated by the use of the "Ussing Chamber method" described in Respirat. Environ. Exercice Physiol. 49, 1027–1031 (1980).

In this method pieces of pig trachea are kept alive in physiological saline medium. The outlets of tracheal glands are observed via a light microscope. The mucus output is triggered either by electric stimulation or by addition of pilocarpine to the incubation medium. The number and the surface of mucus hillocks are recorded via a video tape recorder. The addition of the compounds of formula I in the incubation medium at a concentration of only $10^{-4}$M or less modifies the number and the surface of hillocks reflecting a change in mucus secretion.

The compounds of formula I also have properties of preventing the hepatic necrosis and of immunomodulation.

The hepatic antinecrotic properties of these substances can be demonstrated by the galactosamine hepatitis test in the rat and the carbontetrachloride hepatitis test in the mouse. The galactosamine hepatitis in the rat is a well-known model to faithfully reproduce the morphological and biochemical changes of the human viral hepatitis [K. Decker et al., Adv. enzyme regul. 11, 205 (1973)].

Rats treated intraperitoneally or orally with doses of the compounds of formula I varying from 10 to 200 mg/kg are protected from the hepatic necrosis induced with galactosamine or carbontetrachloride. The hepatic effect is assessed by dosage of plasma transaminases and by measuring the sleeping time induced by pentobarbital which reflects liver function.

The immunomodulation properties of these substances can be demonstrated by a battery of tests classically used in immunology:

(a) humoral immunity test: production of antibodies against the bovine albumine in the mouse. Compounds of formula I, administrated at a dose of 10 to 100 mg/kg, 15 minutes after the antigen (bovine albumine), stimulate the antibody production against this antigen, as measured 15 to 28 days later by the passive hemagglutination technique.

(b) cellular immunity test: delayed hypersensitivity reaction to sheep red blood cells in mice. Compounds of formula I administered at a dose of 10 to 100 mg/kg by subcutaneous route at the same time as the antigen stimulate the delayed hypersensitivity reaction triggered off 21 days later by a subcutaneous injection of the antigen.

(c) cytotoxicity test of mice macrophages against tumoral cells. The macrophages collected from mice having been treated by doses of 10 to 100 mg/kg of compounds of formula I, have a stimulated cytotoxicity against tumoral target cells.

These tests establish that the three main processes involved in the immunological defence (humoral immunity, cellular immunity and macrophages) are modified by the action of compounds of formula I and demonstrate their immunomodulating properties.

These various properties particularly designate the compounds of formula I for the treatment in mammals of acute and chronic diseases induced by viruses, toxins or alcohol. As a matter of fact, during these diseases, the impairment of the hepatic functions results essentially from the hepatic necrosis. This alterations can be diminished by the new substances.

The stimulation of the immunologic defences induced by these substances is useful for the treatment in mammals of the acute and chronic viral hepatitis and also for the treatment of all cases when there is an alteration of immunologic defense reactions such as repeating bacterial or viral infections or carcinogenous diseases. In the latter case, the interest of the substances is specifically demonstrated by the activation of cytotoxic effect of macrophages for tumoral cells.

Compounds of formula I are also able to diminish an increased microvascular permeability and therefore are very potent antioedamators agents in mammals. Thus they can be used e.g. in the treatment of venous diseases.

Increased microvascular permeability with generalized oedema can be induced in rats by administration of galactosamine and dextran.

At doses administrated parenterally or orally varying from 10 to 500 mg/kg compounds of formula I prove to be able to reduce the oedema as measured by the reduction in the accumulation of $I^{125}$ labelled albumine in paws of animals which receive previously an i.v. injection of $I^{125}$ albumine. This measurement is an estimation of the micro-vascular permeability as reported by O. P. Gulati et al., Archives Int. de Pharmacodynamie et de Thérapie 263, 272–287 (1983).

The invention relates especially to pharmaceutical preparations containing compounds of formula I, wherein ring A is unsubstituted or substituted by 1 or 2 substituents selected from the group comprising lower alkyl, hydroxy, lower alkoxy, lower alkylenedioxy, lower alkanoyloxy, halogen, lower alkylamino, di-lower alkylamino, lower alkanoylamino, lower alkanoyl, carboxy and lower alkoxycarbonyl, $R_1$ and $R_2$, independently of one another, each represents hydrogen, lower alkyl or phenyl which is optionally substituted in the same manner as indicated above for the ring A, or $R_1$ and $R_2$ together denote lower alkylene, Y is methylene, methylene monosubstituted by lower alkyl, oxygen, sulfur, sulfinyl or sulfonyl, X represents a bivalent radical —S—C[—B—(Z)$_n$]═CH— the sulfur group S of which is bonded directly to the α- or to the β-position of the bicyclic ring system, B denotes a direct bond, lower alkylene or lower alkenylene, n is 1 or, in case B is lower alkylene or lower alkylene, may be also 2 or 3, and Z represents carboxy, alkoxycarbonyl, carbamoyl which is optionally substituted by one or two equal or different radicals selected from the group comprising lower alkyl, phenyl-lower alkyl wherein the phenyl group is optionally substituted in the same manner as indicated above for the ring A, amino, lower alkylamino and di-lower alkylamino; esterified or amidated carboxy that can be cleaved under physiological conditions; cyano; hydroxycarbamoyl, 5-tetrazolyl, unsubstituted or lower alkyl-substituted 4,5-dihydro-2-oxazolyl; formyl, imino optionally substituted by hydroxy, lower alkoxy, or lower alkanoyloxy, lower alkanoyl optionally substituted by halogen, benzoyl, or phenyl-lower alkanoyl the latter two radicals being optionally substituted in the phenyl ring as indicated above for the ring A, sulfo, lower alkoxysulfonyl, sulfamoyl, lower alkylsulfamoyl, di-lower alkylsulfamoyl, hydroxy, lower alkoxy, alkanoyloxy, amino, lower alkylamino, di-lower alkylamino, lower alkyleneamino, N-morpholino, N-thiomorpholino, N-piperazino which is optionally substituted by lower alkyl at its nitrogen atom in 4-position, lower alkanoylamino, halo-lower alkanoylamino, nitro or halogen;

or tautomeres, stereoisomers or optical isomers thereof, or mixtures of these optical isomers; or pharmaceutically acceptable salts thereof.

The invention relates specifically to pharmaceutical preparations containing compounds of formula I, wherein ring A is unsubstituted or monosubstituted by lower alkyl, hydroxy, lower alkoxy or halogen, $R_1$ and $R_2$, independently of one another, each represents hydrogen, lower alkyl or phenyl which is unsubstituted or monosubstituted in the same manner as indicated for the ring A, or $R_1$ and $R_2$ together denote lower alkylene, Y is methylene, methylene monosubstituted by lower alkyl, oxygen, sulfur, sulfinyl or sulfonyl, X represents a bivalent radical —S—C[—B—(Z)$_n$]═CH— the sulfur group S of which is bonded directly to the α- or to the β-position of the bicyclic ring system, B denotes a direct bond, (C$_1$–C$_4$)alkylene or (C$_2$–C$_4$)alkenylene, n is 1, and Z represents carboxy, C$_1$–C$_{10}$-alkoxycarbonyl, carbamoyl, lower alkylcarbamoyl, di-lower alkylcarbamoyl, phenyl-lower alkylcarbamoyl wherein the phenyl group is unsubstituted or monosubstituted in the same manner as indicated for the ring A, amino-carbamoyl, cyano, 5-tetrazolyl, formyl, imino optionally substituted by hydroxy or lower alkanoyloxy, hydroxy, lower alkoxy, C$_1$–C$_{20}$-alkanoyloxy, amino, lower alkylamino, di-lower alkylamino, lower alkanoylamino, halo-lower alkanoylamino, or halogen;

or tautomeres, stereoisomers or optical isomers thereof, or mixtures of these optical isomers; or pharmaceutical acceptable salts thereof.

The invention relates in particular to pharmaceutical preparations containing compounds of formula I, wherein ring A is unsubstituted or monosubstituted by lower alkyl, hydroxy, lower alkoxy or halogen, $R_1$ and $R_2$, independently of one another, each represents hydrogen, lower alkyl, phenyl or hydroxy-phenyl, or $R_1$ and $R_2$ together denote lower alkylene, Y is methylene, oxygen or sulfur, X represents a bivalent radical —S—C[—B—(Z)$_n$]═CH— the sulfur group S of which is bonded directly to the α-position of the bicyclic ring system, B denotes a direct bond, (C$_1$–C$_4$)alkylene or (C$_2$–C$_4$)alkenylene, n is 1, and Z represents carboxy, C$_1$–C$_8$-alkoxycarbonyl, carbamoyl, lower alkylcarbamoyl, phenyl-lower alkylcarbamoyl, halo-phenyl-lower alkylcarbamoyl, amino-carbamoyl, cyano, 5-tetrazolyl, formyl, imino substituted by hydroxy or lower alkanoyloxy, hydroxy, C$_1$–C$_{16}$-alkanoyloxy, amino or halo-lower alkanoylamino; or tautomeres, stereoisomers or optical isomers thereof, or mixtures of these optical isomers; or pharmaceutically acceptable salts thereof.

The invention further relates to the use of the compounds of formula I for the manufacture of pharmaceutical preparations or as pharmacologically active compounds.

The invention also relates to novel compounds of formula I

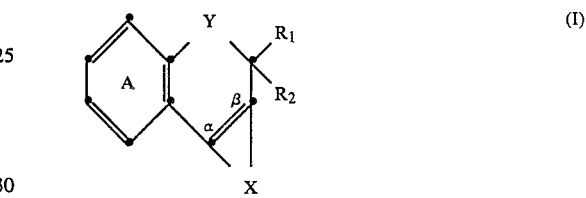

wherein ring A is unsubstituted or substituted, $R_1$ and $R_2$, independently of one another, each represents hydrogen, lower alkyl, aryl or heteroaryl, or $R_1$ and $R_2$ together represent lower alkylene optionally interrupted by oxygen, sulfur or optionally substituted nitrogen, Y is methylene, oxygen, sulfur, sulfinyl or sulfonyl, X represents a bivalent radical —S—C[—B—(Z)$_n$]═CH— the sulfur group S of which is bonded directly to the α- or to the β-position of the bicyclic ring system, B denotes a direct bond, alkylene or alkenylene; n is 1 or, in case B is alkylene or alkenylene, may be also 2 or 3; and Z represents free or functionally modified carboxy, masked carboxy that can be cleaved under physiological conditions, free or functionally modified formyl, acyl, free or functionally modified sulfo, free, etherified or esterified hydroxy, free, etherified or oxidised etherified mercapto, unsubstituted or substituted amino, ammonio, nitro or halogen; with the proviso that $R_1$ is aryl or heteroaryl, if $R_2$ represents hydrogen, Y denotes methylene, X is (α)—S—C(—Z)═CH—(β) wherein Z denotes carboxy, functionally modified carboxy or masked carboxy that can be cleaved under physiological conditions, and ring A is unsubstituted or substituted by 1 or 2 substituents selected from the group comprising halogen and lower alkyl or by the bivalent substituent —(CH$_2$)$_3$— or —(CH$_2$)$_4$— linked to the ring A in two adjacent positions, that ring A is substituted, if $R_1$ and $R_2$ both are hydrogen, Y represents oxygen or sulfur and X is (α)—S—C(—COOH)═CH—(β), and that Y is oxygen, sulfur, sulfinyl or sulfonyl, if $R_1$ and $R_2$ both are hydrogen, X is (α)—S—C(—Z)═CH—(β) wherein Z denotes carboxy, ethoxycarbonyl, cyano, formyl, acetyl, nitro or bromo, and ring A is unsubstituted or monosubstituted in 7-position by methoxy or acetyl;

or tautomers, stereoisomers or optical isomers thereof, or mixtures of these optical isomers; and salts thereof.

Preferred are the compounds of formula I, wherein ring A is unsubstituted or substituted by 1 or 2 substituents selected from the group comprising lower alkyl, hydroxy, lower alkoxy, lower alkylenedioxy, lower alkanoyloxy, halogen, lower alkylamino, di-lower alkylamino, lower alkanoylamino, lower alkanoyl, carboxy and lower alkoxycarbonyl, $R_1$ and $R_2$, independently of one another, each represents hydrogen, lower alkyl or phenyl which is optionally substituted in the same manner as indicated above for the ring A, or $R_1$ and $R_2$ together denote lower alkylene, Y is methylene, oxygen, sulfur, sulfinyl or sulfonyl, X represents a bivalent radical —S—C[—B—(Z)$_n$]═CH— the sulfur group S of which is bonded directly to the α- or to the β-position of the bicyclic ring system, B denotes a direct bond, lower alkylene or lower alkenylene, n is 1 or, in case B is lower alkylene or lower alkenylene, may be also 2 or 3, and Z represents carboxy, alkoxycarbonyl, carbamoyl which is optionally substituted by one or two equal or different radicals selected from the group comprising lower alkyl, phenyl-lower alkyl wherein the phenyl group is optionally substituted in the same manner as indicated above for the ring A, amino, lower alkylamino and di-lower alkylamino; esterified or amidated carboxy that can be cleaved under physiological conditions; cyano; hydroxycarbamoyl, 5-tetrazolyl, unsubstituted or lower alkyl-substituted 4,5-dihydro-2-oxazolyl; formyl, imino optionally substituted by hydroxy, lower alkoxy, or lower alkanoyloxy, lower alkanoyl optionally substituted by halogen, benzoyl, or phenyl-lower alkanoyl the latter two radicals being optionally substituted in the phenyl ring as indicated above for the ring A, sulfo, lower alkoxysulfonyl, sulfamoyl, lower alkylsulfamoyl, di-lower alkylsulfamoyl, hydroxy, lower alkoxy, alkanoyloxy, amino, lower alkylamino, di-lower alkylamino, lower alkyleneamino, N-morpholino, N-thiomorpholino, N-piperazino which is optionally substituted by lower alkyl at its nitrogen atom in 4-position, lower alkanoylamino, halo-lower alkanoylamino, nitro or halogen; with the proviso that $R_1$ is phenyl unsubstituted or substituted as defined above, if $R_2$ represents hydrogen, Y denotes methylene and X is (α)—S—C(—Z)═CH—(β) wherein Z denotes carboxy, functionally modified carboxy or masked carboxy as defined above, that ring A is substituted as defined above, if $R_1$ and $R_2$ both are hydrogen, Y represents oxygen or sulfur and X is (α)—S—C(—COOH)═CH—(β), and that Y is oxygen, sulfur, sulfinyl or sulfonyl, if $R_1$ and $R_2$ both are hydrogen, X is (α)—S—C(—Z)═CH—(β) wherein Z denotes carboxy, ethoxycarbonyl, cyano, formyl, acetyl, nitro or bromo, and ring A is unsubstituted or monosubstituted in 7-position by methoxy or acetyl;

or tautomeres, stereoisomers or optical isomers thereof, or mixtures of these optical isomers; and pharmaceutically acceptable salts thereof.

Greatly preferred are compounds of formula I, wherein ring A is unsubstituted or monosubstituted by lower alkyl, hydroxy, lower alkoxy or halogen, $R_1$ and $R_2$, independently of one another, each represents hydrogen, lower alkyl or phenyl which is unsubstituted or monosubstituted in the same manner as indicated for the ring A, or $R_1$ and $R_2$ together denote lower alkylene, Y is methylene, oxygen, sulfur, sulfinyl or sulfonyl, X represents a bivalent radical —S—C[—B—(Z)$_n$]═CH— the sulfur group S of which is bonded directly to the α- or to the β-position of the bicyclic ring system, B denotes a direct bond, (C$_1$-C$_4$)alkylene or (C$_2$-C$_4$)alkenylene, n is 1, and Z represents carboxy, C$_1$-C$_{10}$-alkoxycarbonyl, carbamoyl, lower alkylcarbamoyl, di-lower alkylcarbamoyl, phenyl-lower alkylcarbamoyl wherein the phenyl group is unsubstituted or monosubstituted in the same manner as indicated for the ring A, amino-carbamoyl, cyano, 5-tetrazolyl, formyl, imino optionally substituted by hydroxy or lower alkanoyloxy, hydroxy, lower alkoxy, C$_1$-C$_{20}$-alkanoyloxy, amino, lower alkylamino, di-lower alkylamino, lower alkanoylamino, halo-lower alkanoylamino, or halogen; with the proviso that $R_1$ is phenyl unsubstituted or substituted as defined above, if $R_2$ represents hydrogen, Y denotes methylene and X is (α)—S—C(—Z)═CH—(β) wherein Z denotes carboxy or functionally modified carboxy as defined above, that ring A is substituted as defined above, if $R_1$ and $R_2$ both are hydrogen, Y represents oxygen or sulfur and X is (α)—S—C(—COOH)═CH—(β), and that Y is oxygen, sulfur, sulfinyl or sulfonyl, if $R_1$ and $R_2$ both are hydrogen, X is (α)—S—C(—Z)═CH—(β) wherein Z denotes carboxy, ethoxycarbonyl, cyano, formyl or bromo, and ring A is unsubstituted or monosubstituted in 7-position by methoxy;

or tautomeres, stereoisomers or optical isomers thereof, or mixtures of these optical isomers; and pharmaceutically acceptable salts thereof.

Primarily preferred are compounds of formula I, wherein ring A is unsubstituted or monosubstituted by lower alkyl, hydroxy, lower alkoxy or halogen, $R_1$ and $R_2$, independently of one another, each represents hydrogen, lower alkyl, phenyl or hydroxy-phenyl, or $R_1$ and $R_2$ together denote lower alkylene, Y is methylene, oxygen or sulfur, X represents a bivalent radical —S—C[—B—(Z)$_n$]═CH— the sulfur group S of which is bonded directly to the α-position of the bicyclic ring system, B denotes a direct bond, (C$_1$-C$_4$)alkylene or (C$_2$-C$_4$)alkenylene, n is 1, and Z represents carboxy, C$_1$-C$_8$-alkoxycarbonyl, carbamoyl, lower alkylcarbamoyl, phenyl-lower alkylcarbamoyl, halo-phenyl-lower alkylcarbamoyl, amino-carbamoyl, cyano, 5-tetrazolyl, formyl, imino substituted by hydroxy or lower alkanoyloxy, hydroxy, C$_1$-C$_{16}$-alkanoyloxy, amino or halo-lower alkanoylamino; with the proviso that $R_1$ is phenyl or hydroxy-phenyl, if $R_2$ represents hydrogen, Y denotes methylene and X is (α)—S—C(—Z)═CH—(β) wherein Z denotes carboxy or functionally modified carboxy as defined above, that ring A is substituted as defined above, if $R_1$ and $R_2$ both are hydrogen, Y represents oxygen or sulfur and X is (α)—S—C(—COOH)═CH—(β), and that Y is oxygen or sulfur, if $R_1$ and $R_2$ both are hydrogen, X is (α)—S—C(—Z)═CH—(β) wherein Z denotes carboxy, ethoxycarbonyl, cyano or formyl, and ring A is unsubstituted or monosubstituted in 7-position by methoxy;

or tautomeres, stereoisomers or optical isomers thereof, or mixtures of these optical isomers; and pharmaceutically acceptable salts thereof.

Further preferred are the compounds of formula I, wherein ring A is unsubstituted or monosubstituted by lower alkyl, lower alkoxy or halogen, $R_1$ denotes phenyl, $R_2$ represents hydrogen, Y is methylene, oxygen or sulfur, X represents a bivalent radical —S—C-[—B—(Z)$_n$]=CH— the sulfur group S of which is bonded directly to the α- or to the β-position of the bicyclic ring system, B denotes a direct bond, (C$_1$-C$_4$)alkylene or (C$_2$-C$_4$)alkenylene, n is 1, and Z represents carboxy, C$_1$-C$_8$-alkoxycarbonyl, carbamoyl, aminocarbamoyl, cyano, 5-tetrazolyl, formyl, imino substituted by hydroxy or lower alkanoyloxy, hydroxy, C$_1$-C$_{16}$-alkanoyloxy, or amino, or furthermore lower alkylcarbamoyl; or tautomeres, stereoisomers or optical isomers thereof, or mixtures of these optical isomers; and pharmaceutically acceptable salts thereof. Compounds as just mentioned above but having Y=methylene mono- or disubstituted, especially monosubstituted, by lower alkyl and R$_1$=phenyl or lower alkyl form also a part of the invention.

Also preferred are the compounds of formula I, wherein ring A is unsubstituted or monosubstituted by lower alkyl, lower alkoxy or halogen, R$_1$ denotes phenyl, R$_2$ represents hydrogen, Y is methylene, oxygen or sulfur, X represents a bivalent radical —S—C-[—Z]=CH— the sulfur group S of which is bonded directly to the α-position of the bicyclic ring system, Z represents carboxy, C$_1$-C$_8$-alkoxycarbonyl, carbamoyl, cyano, 5-tetrazolyl or hydroxymethyl, or furthermore lower alkylcarbamoyl; or tautomeres, stereoisomers or optical isomers thereof, or mixtures of these optical isomers; and pharmaceutically acceptable salts thereof.

Another embodiment of this invention relates to the novel compounds of formula I mentioned above including all sub-groups thereof given above, wherein—by not regarding the provisos given there—Y is oxygen, sulfur, sulfinyl or sulfonyl, if R$_1$ represents hydrogen and R$_2$ is hydrogen or lower alkyl; and Y represents sulfinyl or sulfonyl only, if, in addtion, ring A is unsubstituted and X denotes (α)—S—C(—COOH)=CH—(β).

The preferences given below are likewise valid for pharmaceutical preparations containing compounds of formula I as well as novel compounds of formula I.

Preferred are compounds of formula I wherein R$_1$ and R$_2$ represent two methyl radicals, one hydrogen and one phenyl, or together 1,5-pentylene; furthermore one hydrogen and one hydroxy-phenyl, and also two hydrogen radicals; with special emphasis on those compounds of formula I wherein R$_1$ and R$_2$ represent one hydrogen and one phenyl.

Preferred are compounds of formula I wherein Y represents oxygen, sulfur, sulfinyl or sulfonyl, further methylene; and in particular oxygen or sulfur.

Also preferred are the compounds of formula I wherein X represents a bivalent radical —S—C[—B—(Z)$_n$]=CH— the sulfur group S of which is bonded directly to the α-position of the bicyclic ring system. Emphasis should be placed on compounds of formula I wherein B is a direct bond, methylene or ethenylene, e.g. 1,2-ethenylene, and especially on those wherein B represents a direct bond. Within the compounds of formula I wherein B is alkylene or alkenylene are those of particular importance wherein n is 1.

Of great importance are the compounds of formula I wherein the radical —B—(Z)$_n$ represents carboxy, C$_1$-C$_8$-alkoxycarbonyl, carbamoyl, lower alkylcarbamoyl, phenyl-lower alkylcarbamoyl, halo-phenyl-lower alkylcarbamoyl, cyano, 5-tetrazolyl, formyl, halo-lower alkanoylamino, hydroxymethyl, C$_1$-C$_{16}$-alkanoyloxymethyl, aminomethyl, carboxymethyl or 2-carboxyethenyl; and of greatest interest are those, wherein —B—(Z)$_n$ is carboxy or carbamoyl.

Above all are preferred the compounds of formula I described in the examples and pharmaceutically acceptable salts thereof.

The invention also relates to pharmaceutical preparations containing the novel compounds of formula I or any of the preferred embodiments thereof as described above.

Compounds of the formula I can be produced by processes known per se.

Thus, novel compounds of formula I, wherein B is a direct bond and Z represents free or functionally modified carboxy, free or functionally modified formyl, masked carboxy that can be cleaved under physiological conditions, acyl, free or functionally modified sulfo, oxidised etherified mercapto or nitro, can be prepared e.g. (a) by reacting a compound of formula II

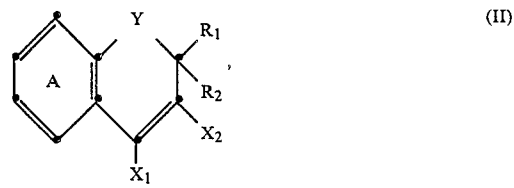

wherein one of the radicals X$_1$ and X$_2$ represents a leaving group and the other is free or modified formyl, with a compound of formula III

or an alkali metal mercaptide salt thereof, wherein Z has meaning as defined above.

Novel compounds of formula I wherein B is alkylene or alkenylene and Z has meaning as defined under formula I, or wherein B is a direct bond and Z represents free or functionally modified carboxy, free or functionally modified formyl, masked carboxy that can be cleaved under physiological conditions, acyl, free or functionally modified sulfo, oxidised etherified mercapto or nitro, can be prepared e.g. (a') by reacting a compound of formula II as defined above with a compound of formula IIIa

or an alkali metal mercaptide salt thereof, wherein Z and n have meaning as defined under formula I and L represents a radical that activates the adjacent group CH for reaction with the free or modified formyl group X$_1$ and X$_2$ respectively of formula II and that, in addition, is—optionally after one or more consecutive reaction steps—split off during the reaction.

Novel compounds of formula I can also be prepared e.g. (b) by converting in a compound of formula IV

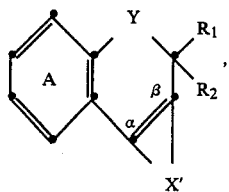

wherein X' represents a bivalent radical —S—C—[—M]=CH— the sulfur group of which is bonded directly to the α- or to the β-position of the bicyclic ring system and M is a radical convertible into a group —B—(Z)$_n$, the radical M into a group —B—(Z)$_n$.

Furthermore, a resulting compound of formula I can be converted into a different compound of formula I, and/or a resulting salt can be converted into the free compound or into a different salt, and/or a resulting free compound of the formula I having salt-forming properties can be converted into a salt, and/or a resulting mixture of stereoisomers or optical isomers, such as a diastereoisomeric mixture, can be separated into the individual stereoisomers, optical isomers or enantiomeric mixtures, respectively, and/or resulting enantiomeric mixtures, such as a racemate, can be split into the optical isomers.

A leaving group $X_1$ or $X_2$, respectively, in a compound of formula II according to process a)/a') is in particular halogen, e.g. chloro or bromo, but may be also e.g. hydroxy, lower alkoxy, lower alkanoyloxy, mercapto, lower alkylthio, unsubstituted or substituted amino, ammonio or a pyridinium salt [For the latter cp. J. Prakt. Chem. 314, 499 (1972)].

A free or modified formyl group $X_1$ and $X_2$, respectively, in a compound of formula II according to process a)/a') is especially formyl, but may be also e.g. imino optionally substituted by e.g. lower alkyl or phenyl, or an iminium salt, especially a di-lower alkyliminium salt.

If $X_1$ represents a leaving group and $X_2$ is free or modified formyl in a compound of formula II the process a)/a') leads to compounds of formula I wherein the sulfur group S of the bivalent radical —S—C—[—B—(Z)$_n$]=CH— is bonded directly to the α-position of the bicyclic ring system. If the meanings of $X_1$ and $X_2$ are exchanged, the reverse compounds of formula I wherein the sulfur group S is bonded directly to the β-position are obtained.

Activation of the CH$_2$ group in formula III for the aldol condensation type reaction is achieved by the group Z as defined there, whereas in formula IIIa activation of the CH group is performed by the radical L which is especially free or functionally modified carboxy, in first instance carboxy, for the requisite of being split off during the reaction.

Thiophene ring formation according to process a)a') may be catalysed either by the presence of acids or preferably of bases. Suitable bases are e.g. alkali metal hydrogencarbonate, such as sodium hydrogencarbonate, alkali metal hydroxide, such as potassium hydroxide, or organic bases, such as tri-lower alkylamines, e.g. triethylamine.

It is also possible to use a precursor of a compound of formula III or IIIa for the process a)/a') which in situ forms the desired compound of formula III or IIIa, e.g. a dimer, such as dimeric mercaptoacetaldehyde, i.e. 2,5-dihydroxy-1,4-dithian.

Starting materials of formula II wherein $X_1$ ($X_2$) is chloro and $X_2$ ($X_1$) represents formyl are known [cp. for example Bollettino 27, 279 (1969), Indian J. Chem. 20B, 243 (1981)] or, if novel, can be prepared analogous to known compounds e.g. by reacting corresponding bicyclic keto compounds of formulae V or Va,

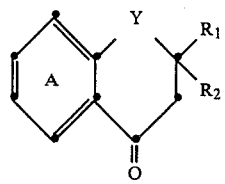

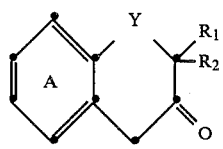

such as 1- or 2-tetralones or 3- or 4-thio)chromanones and the like, e.g. with phosphorous oxychloride and dimethylformamide (Vilsmeier-Haack). This reaction passes through intermediate iminium salts which can be isolated and also used for a reaction according to process a)/a') [cp. J. Prakt. Chem. 318, 731 (1976)]. In the European patent application 139,615, further starting materials of formula II as well as details concerning this reaction are described. In the European patent application 140,830, preparation of starting materials of formula II wherein $X_1$ ($X_2$) is a leaving group different from halogen and/or $X_2$ ($X_1$) represents modified formyl instead of formyl is described. Such compounds are preferably prepared starting from the corresponding haloformyl compounds of formula II described above. Leaving groups different from halogen are introduced preferably by nucleophilic displacement of a halogen radical, e.g. lower alkoxy, lower alkylthio, unsubstituted or substituted amino or ammonio by reaction with lower alkanols or lower alkylmercaptanes, especially alkali metal salts thereof, ammonia or primary, secondary or tertiary amines. On the other hand, modified formyl is obtained preferably starting from formyl using well-known procedures, e.g. those of imine preparation.

Starting materials of formulae V and Va are known or can be prepared in analogy to known compounds. Particulars for the preparation of these compounds can be found e.g. in: The Chemistry of Heterocyclic Compounds, Vol. 31, G. P. Ellis (Ed.), "Chromenes, Chromanones and Chromones", New York 1977, pp. 207–428 and pp. 193–206. For example, cyclisation of 3-phenylthio(oxy)propionic acids optionally further mono- or disubstituted in 3-position leads to 4-(thio)chromanones of formula V [cp. J. Amer. Chem. Soc. 76, 5065 (1954)]. Cyclisation of ethenyl-(2-hydroxyphenyl)ketones optionally further mono- or disubstituted in 2-position of ethenyl yields 4-chromanones of formula V. Dieckmann condensation of lower alkyl 2-lower alkoxycarbonylmethylphenyloxy(or thio)-acetate optionally further mono- or disubstituted in 2-position of the acetate radical leads to 3-(thio)chromanones which are substituted in 4- or 2-position respectively by a lower alkoxycarbonyl group. The latter can be split off by first hydrolysing e.g. with a base and then decarboxylatng e.g. with copper in quinoline. Analogously, Dieckmann condensation of e.g. lower alkyl 3-(2-lower alkoxycarbonylmethylphenyl)propionates finally yields 2-tetralones. The synthesis of 1-tetralones is described e.g. in J. Amer. Chem. Soc. 89, 386 (1967). Further references describing useful methods of preparing compounds of formula V are e.g.: Synthesis 1980, 725; Synthesis 1978, 886 and Angew. Chem. 94, 254 (1982).

Compounds of formulae III and IIIa are known or, if novel, can be prepared analogous to known compounds. A preferred method of introducing the mercapto group into these molecules is to react corresponding halo-substituted compounds with a reagent capable of introducing mercapto, such as sodium hydrogensulfide. The halo-substituted compounds mentioned are in many cases e.g. obtainable by direct halogenation of the corresponding unsubstituted compounds.

Radicals M convertible into a group $-B-(Z)_n$ in a compound of formula IV according to process (b) are preferably hydrogen, an organometallic group or lower alkyl, but also e.g. lower alkenyl.

Compounds of formula IV wherein M represents hydrogen can be subjected to any kind of normal aromatic electrophilic substitution reactions, such as halogenation, especially bromination, e.g. with bromine and acetic acid, nitration, Friedel-Crafts acylation, such as acetylation, e.g. with acetyl chloride, or formylation, e.g. with phosphorous oxychloride and dimethylformamide, yielding compounds of formula I wherein the group $-B-(Z)_n$ corresponds to halogen, acyl, nitro or formyl, respectively [cp. J. Chem. Soc. Perkin Tr. 1 1977, 63]. Furthermore, introduction of a di-lower alkylaminomethyl group, can be achieved e.g. by reacting a compound of formula I wherein M is hydrogen with N,N-di-lower alkyl-methylene-ammonium halide according to Synthesis 1983, 73.

Compounds of formula IV wherein M is lower alkyl, especially methyl, can be reacted e.g. with halogenating agents, such as chlorine, bromine, N-chloro-, N-bromosuccinimide or metal fluorides, such as antimony tri- or pentafluoride, to yield compounds of formula I wherein the group $-B-(Z)_n$ corresponds to $\alpha$-halo-, $\alpha,\alpha$-dihalo- or $\alpha,\alpha,\alpha$-trihalo-lower alkyl, e.g. $\alpha$-bromoethyl, chloromethyl, dichloromethyl, trichloro- or trifluoromethyl. Furthermore, said compounds of formula IV, wherein M is lower alkyl, especially methyl, can be oxidised to compounds of formula I wherein the group $-B-(Z)_n$ is hydroxymethyl or especially formyl or carboxy, by methods well-known to the art.

An organometallic group M is preferably a lithium radical or a halomagnesium group, but may also be e.g. a copper-containing group. Compounds of formula IV wherein M is an organometallic group may be subjected to any of the usual reactions with participation of organometallic compounds, for example reactions with compounds containing carbonyl groups or compounds containing halogen radicals. Thus, reaction with e.g. carbon dioxide yields a compound of formula I wherein the group $-B-(Z)_n$ is carboxy, or reaction with e.g. a compound containing a formylalkyl group results in a compound of formula I wherein B is alkenylene [cp. J. Heterocycl. Chem. 19, 871 (1982)].

Compounds of formula IV wherein M is hydrogen, lower alkyl or lower alkenyl can be prepared e.g. analogous to process a') by reacting a compound of formula II with a compound of formula IIIa wherein L is e.g. lower alkoxycarbonyl and the group $-B-(Z)_n$ represents hydrogen, lower alkyl or lower alkenyl, respectively. Subsequently, the group L is splitt off by first hydrolysing e.g. with alkali metal hydroxide or alkoxide and then decarboxylating e.g. with copper in quinoline at elevated temperature, such as 210° C., to yield the desired compounds of formula IV. Compounds of formula IV wherein M is an organometallic group can be obtained from e.g. corresponding compounds of formula IV wherein M is hydrogen by reaction with a metallising agent, e.g. with lithium, magnesium, copper(I) halides and/or especially with n-butyllithium.

Compounds of formula IV wherein M is lower alkenyl, especially ethenyl (vinyl), can be subjected e.g. to ozonolysis yielding compounds of formula I wherein the group $-B-(Z)_n$ is formyl. Furthermore, said compounds of formula IV wherein M is e.g. ethenyl, may be treated e.g. with nickel carbonyl and carbon monoxide under high pressure conditions to yield compounds of formula I wherein the group $-B-(Z)_n$ corresponds to e.g. 2-carboxyethenyl.

Compounds of formula I can be converted into different compounds of formula I in a manner known per se.

Compounds of formula I wherein Z represents hydroxy and B preferably is a direct bond but may be also alkylene or alkenylene, can be obtained e.g. from other compounds of formula I wherein Z is formyl or acyl in a two-step synthesis. Treatment of the formyl (or acyl) compound with a peracid according to a Bayer-Villiger reaction leads to the corresponding compound of formula I wherein Z is formyloxy (or acyloxy). This may be hydrolysed e.g. using preferably a basic catalyst, e.g. sodium hydroxide, to the free hydroxy compound.

The peracid used may be organic, e.g. peracetic acid, trifluoroperacetic acid, perbenzoic acid, p-nitroperbenzoic acid or m-chloroperbenzoic acid, or inorganic, such as persulfuric acids, e.g. monopersulfuric acid. The peracids used may also be formed in situ, e.g. by reacting the corresponding acid with hydrogen peroxide.

Compounds of formula I wherein Z is etherified hydroxy can be obtained by usual etherization methods starting from corresponding compounds of formula I wherein Z is hydroxy. For instance, lower alkoxy is obtained e.g. by reaction with a reactive ester of a lower alkanol, such as a lower alkyl halide, a di-lower alkylsulfate or lower alkyl- or optionally substituted phenylsulfonic acid lower alkylester, advantageously in the presence of a basic agent, such as an alkali metal hydroxide, carbonate or alcoholate, for example sodium or potassium hydroxide, potassium carbonate or sodium methoxide, or a tertiary organic nitrogen base, such as a tri-lower alkylamine, for example triethylamine, or pyridine.

Compounds of formula I wherein Z is etherified hydroxy, e.g. lower alkoxy as well as phenyloxy or heterocyclyloxy, and B is alkylene can also be obtained e.g. by reaction of a compound of formula I wherein Z is a reactive ester of hydroxy as indicated above for a lower alkanol with a hydroxy-substituted hydrocarbon, e.g. a lower alkanol, the appropriate phenol or hydroxyheterocyclyl compound, respectively. If B is a direct bond, compounds of formula I wherein Z e.g. is phenyloxy or heterocyclyloxy can be obtained e.g. by reacting corresponding compounds of formula I wherein Z is hydroxy, preferably as an alkalimetal salt thereof, with e.g. the appropriate halogen-, especially bromo-substituted benzene or heterocyclic compound, respectively, preferably in the presence of copper catalysts, such as copper powder, e.g. according to J. Chem. Soc. 1965, 4953. The inverse reaction starting with a compound of formula I wherein Z is halogen and a hydroxy-substituted benzene or heterocyclic compound, is also possible.

Acylation of compounds of formula I wherein Z is hydroxy to other compounds of formula I wherein Z is acyloxy is effected e.g. by means of a corresponding acid anhydride or chloride, such as acetanhydride, benzoyl chloride or phenylacetyl chloride.

Compounds of formula I wherein Z represents mercapto and B preferably is a direct bond but may be also alkylene or alkenylene, can be prepared e.g. by reducing a compound of formula I wherein Z represents sulfonyl chloride, for example with zinc dust and hydrochloric acid, or stannous chloride, or preferably with lithium aluminium hydride.

Compounds of formula I wherein Z represents etherified mercapto can be obtained e.g. in complete analogy to the corresponding etherified hydroxy compounds described above by using starting materials that contain mercapto in place of hydroxy. For instance, compounds of formula I wherein B is a direct bond and Z is phenylthio or heterocyclylthio are prepared e.g. by reacting corresponding compounds of formula I wherein Z is mercapto with the appropriate halogen-substituted benzene or heterocyclic compound, respectively (cp. GB—A—1,459,571).

Compounds of formula I wherein —B—(Z)$_n$ represents mercapto can also be obtained e.g. from other compounds of formula I wherein —B—(Z)$_n$ is lower alkylthio using conventional dealkylation methods (cp. Synthesis 1983, 751).

Compounds of formula I wherein Z represents amino and B preferably is a direct bond but may be also alkylene or alkenylene, can be obtained e.g. from corresponding compounds of formula I wherein Z is carbamoyl according to Hofmann or e.g. from corresponding compounds of formula I wherein Z is carboxy according to the Schmidt reaction. In the Hofmann degradation, the carbamoyl compound is reacted with e.g. an alkalimetal hypohalogenite, which preferably is prepared from alkalimetal hydroxide and elemental halogen, such as bromine or chlorine, to yield the corresponding amino compound. The Schmidt reaction is characterised in reacting e.g. the carboxy compound with hydrazoic acid yielding the corresponding amino compound.

Furthermore, compounds of formula I wherein Z is amino and B preferably is a direct bond but may be also alkylene or alkenylene, can be obtained e.g. by reducing corresponding compounds of formula I wherein Z is nitro. Suitable reductions methods are e.g. the catalytical reduction with molecular hydrogen using e.g. Raney nickel as a catalyst, the reduction with hydrazine, iron and hydrochloric acid, sodium dithionite, sodium or ammonium sulfide, tin(II) chloride and the like.

Compounds of formula I wherein Z is amino can be converted into other compounds of formula I wherein Z represents acylamino, mono- or di-lower alkylamino or lower alkyleneamino, aza, oxa- or thia-lower alkyleneamino. Also mono-lower alkylamino Z can be converted into di-lower alkylamino. The acylation is effected, for example, by means of a corresponding acid anhydride or chloride, such as acetanhydride or phenylacetyl chloride. Alkyl(en)ating agents are, for example, reactive esters of a lower alkanol, lower alkanediol or aza, oxa- or thia-lower alkanediol, such as a lower alkyl(enedi)halide, for example, bromide or iodide, lower alkyl(enedi)-sulfonate, for example methanesulfonate or p-toluenesulfonate, or a di-lower alkyl sulfate, for example dimethyl sulfate, preferably under basic conditions, such as in the presence of alkalimetal hydroxide solution and advantageously a phase transfer catalyst, such as tetrabutylammonium bromide or benzyltrimethylammonium chloride. The alkylating agents mentioned above are also useful to convert tertiary amino Z into ammonio. In a entirely analogous manner, also carbamoyl Z can be converted into N-acylcarbamoyl, mono- or di-lower alkylcarbamoyl, lower alkylenecarbamoyl or (aza-, oxa- or thia)-lower alkylenecarbamoyl and mono-lower alkylcarbamoyl can be converted into di-lower alkylcarbamoyl, but stronger basic condensation agents, such as alkali metal amides or alcoholates, for example sodium amide or sodium methoxide, may be necesssary.

Compounds of formula I wherein Z is primary, secondary or tertiary amino including e.g. phenylamino or heterocyclylamino and B is alkylene can be obtained e.g. by reacting a compound of formula I wherein Z is a reactive ester of hydroxy as indicated above and B is alkylene with ammonia, a primary, secondary or tertiary amine, e.g. the appropriate aniline or aminoheterocyclyl compound. If B is a direct bond, compounds of formula I wherein Z e.g. is phenylamino or heterocyclylamino can be obtained e.g. by reacting corresponding compounds of formula I wherein Z is halogen, especially bromo or iodo, or hydroxy, with the appropriate amino-substituted benzene or heterocyclyl compound, respectively, advantageously in the presence of catalysts. If Z is halogen, e.g. copper catalysts, such as copper powder or copper (I) halides are useful [cp. Org. Synth. Coll. Vol. I, 544 (1941)]. If Z is hydroxy, preferred catalysts are calcium chloride, sulfanilic acid, iodine or zinc chloride.

Compounds of formula I wherein B is a direct bond and Z represents 2-phenylhydrazino are e.g. obtained by reduction with e.g. thiourea-S-dioxide ("formamidine sulfinic acid") from corresponding 2-phenylazo compounds which themselves are prepared e.g. by reacting a compound of formula I wherein B is a direct bond and Z is amino with an optionally substituted nitrosobenzene.

Compounds of formula I wherein Z represents chloro or bromo and B preferably is a direct bond but may be also alkylene or alkenylene, can be obtained e.g. from other compounds of formula I wherein Z is carboxy using e.g. a Hundsdiecker degradation-type reaction [cp. Chem. Rev. 56, 219 (1956); Org. React. 9, 332 (1957)]. In these, the carboxy compound first is transferred into a salt, preferably a heavy metal salt, such as a silver salt, and then reacted with elemental halogen, such as bromine, to yield the desired halogen compound. Compounds of formula I wherein Z is carboxy can also be converted to compounds of formula I wherein Z is iodo, e.g. by treatment with iodine, lead tetraacetate and light irradiation.

Compounds of formula I wherein Z represents fluoro and B is a direct bond can be e.g. obtained from other compounds of formula I wherein Z is amino and B is a direct bond by first diazotising the amino compound and preparing the diazonium tetrafluoroborate and then decomposing this salt—e.g. by pyrrolysis or in the presence of small amounts of copper powder—to yield the corresponding fluoro compound (Balz-Schiemann reaction).

Compounds of formula I wherein Z represents chloro, bromo or iodo and B is a direct bond can be e.g.

produced by the Sandmeyer reaction starting from other compounds of formula I wherein Z is amino and B is a direct bond. The latter compounds are diazotised and—optionally in the presence of copper powder or copper(I) salts as a catalyst—are reacted with chloride, bromide or iodide anions to yield compounds of formula I wherein Z is chloro, bromo or iodo, respectively, and B is a direct bond.

Compounds of formula I wherein Z is halogen bonded to a $sp^3$ carbon atom, n is 1 and B is alkylene or alkenylene can be e.g. obtained by conversion of the corresponding compounds of formula I wherein Z is hydroxy using well-known halogenation procedures, such as those with hydrohalic acids, especially hydrobromic or hydroiodic acid, thionyl chloride or bromide, phosphorous trihalide or phosphorous pentahalide, and the like. Analogous compounds of formula I wherein Z is fluoro are e.g. obtained by first treating the corresponding hydroxy compound with e.g. p-toluenesulfonyl chloride and then with e.g. potassium fluoride.

Compounds of formula I wherein Z is e.g. aryl-lower alkoxy, such as benzyloxy, or lower alkoxy can be converted to compounds wherein Z is hydroxy e.g. by hydrogenolysis or hydrolysis respectively, using methods well known in the art.

The compounds of formula I wherein Z represents hydroxycarbamoyl (hydroxamic acids) may be prepared by condensing a compound of formula I, wherein Z represents carboxy or a reactive functional derivative thereof, with hydroxylamine or an acid addition salt thereof, advantageously with hydroxylamine hydrochloride, preferably in the presence of a basic reagent, e.g. sodium hydroxide. Said condensation is carried out according to methods known per se e.g. as described in Barton et al., Comprehensive Organic Chemistry, Vol. 2, pp. 1037–1038 (1979).

The compounds of formula I wherein Z represents 5-tetrazolyl may be prepared e.g. by condensing a compound of formula I, wherein Z represents preferably cyano, with hydrazoic acid or a compound which serves as a source of hydrazoic acid, e.g. a metal or ammonium salt of hydrazoic acid, preferably an alkali metal azide such as sodium azide or ammonium azide. Said condensation is carried out according to methods known per se, e.g. as described in Barton et al., Comprehensive Organic Chemistry Vol. 4, pp. 407–409 (1979), preferably in the presence of an acid, e.g. hydrochloric acid or ammonium chloride.

Said tetrazoles may also be prepared e.g. from a compound of formula I wherein the group Z representing cyano or carbamoyl is first converted to a halo- or lower alkoxyimino group for condensation with e.g. an alkali metal azide or ammonium azide.

The compounds of formula I wherein Z represents 4,5-dihydro-2-oxazolyl or 4,5-dihydro-2-oxazolyl substituted by lower alkyl are preferably prepared by condensing a compound of formula I, wherein Z represents carboxy or a reactive functional derivative thereof, with 2-hydroxyethylamine optionally mono- or di(vicinal or gem)-C-substituted by lower alkyl, or with aziridin optionally mono- or di-(vicinal or gem)-C-substituted by lower alkyl, e.g. 2-aminoethanol, 2-methyl-2-aminopropanol or 2,2-dimethylaziridine. The condensation is carried out according to methods generally known per se, e.g. as described in J. Org. Chem. 39, 2787 (1974). It occurs either spontaneously or in the presence of condensing agents, e.g. disubstituted carbodiimides, such as dicyclohexylcarbodiimide, e.g. in the case where Z represents carboxy.

Compounds of formula I wherein Z is halogen and B is alkylene may be reacted e.g. with a metal cyanide, such as potassium cyanide, in a conventional manner to yield compounds of formula I wherein Z is cyano. These in turn are converted to compounds of formula I wherein Z is carboxy, lower alkoxycarbonyl or carbamoyl using methods known to the art.

Thus, the compounds of formula I wherein Z represents cyano are converted to compounds of formula I wherein Z is carboxy e.g. by hydrolysis with inorganic acids, e.g. a hydrohalic acid such as hydrochloric acid or sulfuric acid in aqueous solution, or advantageously by hydrolysis with aqueous alkali metal hydroxide, e.g. potassium hydroxide.

The conversion of said nitriles to compounds of formula I wherein Z represents lower alkoxycarbonyl is advantageously carried out by treatment first with a lower alkanol, e.g. anhydrous ethanol, in the presence of a strong acid, e.g. hydrochloric acid, followed by careful hydrolysis with water.

Furthermore, the conversion of the said nitriles to compounds of formula I wherein Z represents carbamoyl is e.g. carried out by treatment with an alkali metal hydroxide, e.g. dilute sodium hydroxide, and hydrogen peroxide, preferably at room temperature. Furthermore, compounds of formula I wherein Z is halogen and B is alkylene are converted to compounds of formula I, wherein Z is carboxy and the alkylene chain is extended by one methylene group, by first treating with e.g. a di-lower alkyl malonate, such as diethyl malonate, in the presence of a base such as potassium carbonate or sodium ethoxide. The resulting substituted di-lower alkyl malonate is hydrolyzed, advantageously with aqueous base, such as dilute sodium hydroxide, to the corresponding malonic acid which is decarboxylated under standard conditions, e.g. by heating in xylene solution, to give the desired compound of formula I. Substitution of the di-lower alkyl malonate with a lower alkyl cyanoacetate yields the corresponding compounds of formula I wherein Z is cyano.

Compounds of the invention, wherein B represents alkenylene with a terminal double bond and Z is e.g. lower alkoxycarbonyl, may also be prepared from compounds of formula I wherein B represents alkylene and Z is halogen. For instance, said intermediates are first treated with e.g. a lower alkyl ester of an α-(aryl- or alkyl) thioacetic acid such as ethyl α-(phenylthio)-acetate, in the presence of a strong base such as sodium hydride. Subsequent oxidation of the resulting α-arylthio or α-alkylthio substituted ester to the α-arylsulfinyl or α-alkylsulfinyl ester with e.g. sodium periodate, followed by heat-induced elimination, by e.g. refluxing in xylene, yields a compound of formula I wherein B represents alkenylene with a terminal double bond and Z represents e.g. lower alkoxycarbonyl, and the alkenylene chain has been extended by one carbon atom in comparison to the former alkylene chain. The same transformation is also carried out using e.g. ethyl α-(phenylseleno)acetate as described in J. Am. Chem. Soc. 95, 6137 (1973). Similarly, the compounds of formula I wherein Z represents halogen and B is alkylene may first be converted to the corresponding carboxaldehydes with e.g. dimethylsulfoxide in the presence of triethylamine and silver tetrafluoroborate, or with chromium trioxide and pyridine in methylene chloride. Subsequent Wittig condensation e.g. with trimethylphosphonoacetate or ethyl (triphenylphosphoranylidene)-acetate also yields the above-cited α,β-unsaturated esters.

In general, the Wittig reaction including its modifications can be used to convert a compound of formula I wherein Z is formyl or acyl into another compound of formula I wherein B is alkenylene. The formyl or acyl compound is reacted e.g. with a compound containing a triphenylphosphoranylidene group or a di-lower alkyl-phosphono group.

Compounds of formula I wherein B is alkenylene with a terminal double bond, e.g. α,β-unsaturated esters, may also be prepared from the corresponding α,β-saturated compounds (where B is corresponding alkylene) by treatment with e.g. phenylselenyl chloride in the presence of a strong base according to the procedure described in J. Am. Chem. Soc. 95, 6137 (1973).

Compounds of formula I wherein Z is esterified carboxy, especially lower alkoxycarbonyl, may be amidized with ammonia, mono- or di-lower alkylamines, e.g. methylamine or dimethylamine, to yield compounds of formula I wherein Z represents unsubstituted, mono- or di-lower alkyl-substituted carbamoyl.

Conversion of compounds of formula I wherein Z is functionally modified carboxy, e.g. alkoxycarbonyl; cyano; unsubstituted, mono- or di-(lower alkyl)-substituted carbamoyl or 4,5-dihydro-2-oxazolyl optionally substituted by lower alkyl to compounds of formula I wherein Z represents carboxy is advantageously carried out by hydrolysis with inorganic acids such as hydrohalic or sulfuric acid or with aqueous alkalies, preferably alkali metal hydroxides such as lithium or sodium hydroxide.

Compounds of formula I wherein Z represents carboxy or alkoxycarbonyl may be reduced with simple or complex light metal hydrides such as lithium aluminum hydride, alane or diborane to compounds of formula I wherein Z is hydroxy and the radical B has been extended by one $CH_2$ group. Said alcohols are also obtained e.g. by appropriate solvolysis of compounds of formula I wherein Z is halogen and B is alkylene by treatment with e.g. an alkali metal hydroxide such as lithium or sodium hydroxide.

Said alcohols may in turn be transformed to the compounds of formula I wherein Z is carboxy and the radical B is shortened by one $CH_2$ group, with conventional oxidizing agents, advantageously with pyridinium dichromate in dimethylformamide at room temperature.

Carboxy groups may be esterified e.g. with alkanols such as ethanol in the presence of a strong acid, e.g. sulfuric acid, or with diazo lower alkanes, e.g. diazomethane, to give the corresponding esters, e.g. compounds of formula I wherein Z is (lower) alkoxycarbonyl.

Furthermore, carboxy groups may be converted via treatment of a reactive intermediate thereof, e.g. an acid halide such as the acid chloride, or a mixed anhydride, e.g. such derived from a lower alkyl halocarbonate such as ethyl chloroformate, with ammonia, mono- or di-lower alkylamines, preferably in the presence of a basic catalyst such as pyridine, to compounds of formula I wherein Z represents unsubstituted, mono- or di-lower alkyl-substituted carbamoyl.

Furthermore compounds of formula I wherein B represents alkenylene may be converted by catalytic hydrogenation, advantageously under neutral conditions e.g. with palladium catalyst at atmospheric pressure, to compounds of formula I wherein B represents alkylene.

The carboxaldehydes, i.e. the compounds of formula I wherein Z represents formyl, may be prepared by oxidizing e.g. compounds of formula I wherein Z represents hydroxy or halogen and B is extended by one methylene group in comparison to the final product, with e.g. dimethyl sulfoxide and a catalyst, such as a mixture of triethylamine and silver tetrafluoroborate, or with chromium trioxide and pyridine or other oxidizing agents known in the art. Said carboxaldehydes are converted to the corresponding acetals, i.e. the compounds of formula I wherein Z represents di-lower alkoxymethyl or alkylenedioxymethyl, e.g. a dimethylacetal, by acid-catalyzed condensation with an alcohol, e.g. methanol.

Compounds of formula I wherein Z represents carboxy may be converted by the well known Arndt-Eistert synthesis to compounds of formula I wherein Z represents carboxy and the chain has been extended by 1 carbon atom. More particularly, a reactive functional derivative of the starting carboxylic acid, e.g. the acid chloride, is treated with diazomethane in e.g. diethyl ether to yield a compound of formula I wherein Z represents diazoacetyl. Rearrangement with e.g. silver oxide yields said carboxylic acid for formula I wherein the chain has been extended by 1 carbon atom.

Furthermore, compounds of formula I wherein Z represents acetyl may be oxidatively cleaved to the corresponding compounds of formula I wherein Z represents carboxy e.g. by conversion first to a compound of formula I wherein Z represents trihaloacetyl, e.g. tribromoacetyl, by treatment e.g. with sodium hypobromite followed by cleavage with e.g. an aqueous base, such as sodium hydroxide.

Compounds of formula I wherein Z represents acetyl are e.g. prepared by condensing a compound of formula I wherein Z is cyano with an organometallic methane derivative, e.g. methyl magnesium bromide or methyl lithium, under standard conditions.

Compounds of formula Ia wherein Z represents formyl, di-lower alkoxymethyl or alkylenedioxymethyl (formyl protected in the form of an acetal), e.g. the dimethyl acetal, are oxidized with e.g. silver nitrate, pyridinium dichromate or ozone to the corresponding compound of formula I wherein Z represents carboxy.

Compounds of formula I wherein Z represents halogen may be converted to a correponding organometallic intermediate, e.g. a cuprous, lithium or magnesium derivative, under conditions well known to the art.

Condensation of e.g. the resulting organomagnesium (Grignard) reagent with carbon dioxide yields a compound of formula I wherein Z represents carboxy. Condensation of said Grignard reagent with e.g. a lower alkyl haloacetate, e.g. ethyl bromoacetate, and subsequent hydrolysis yields a compound of formula I wherein Z represents carboxy and the radical B has been extended by one $CH_2$ group.

Said Grignard reagent may be condensed in the presence of a cuprous halide, e.g. cuprous chloride, with an α,β-unsaturated acid, e.g. acrylic acid, to yield a compound of formula I wherein Z represents carboxy and wherein the radical B has been extended e.g. by a terminal 1,2-ethylene group.

Compounds of formula I wherein Y is sulfinyl can be produced e.g. by oxidation of corresponding compounds of formula I wherein Y is sulfur in a manner known per se. The oxidation to sulfinyl can be effected for example by inorganic peracids, for example periodic acid or persulfuric acid; organic peracids, such as percarboxylic or persulfonic acids, for example performic, peracetic or trifluoroperacetic acid, m-chloroperbenzoic acid or p-toluenepersulfonic acid; by mixtures consisting of hydrogen peroxide and acids, for example mixtures of hydrogen peroxide and acetic acid.

The oxidation is often carried out in the presence of suitable catalysts, for example suitable optionally substituted carboxylic acids, for example acetic or trifluoroacetic acid, or oxides of transition metals, such as the oxides of the elements of the auxiliary group VII, for example vanadium, molybdenum or tungsten oxide.

Compounds of formula I wherein Y is sulfonyl can be obtained e.g. by oxidation of corresponding compounds of formula I wherein Y is sulfur or sulfinyl, for example with dinitrogentetroxide as a catalyst, in the presence of oxygen, preferably at low temperature, using the same oxidation means as just described above for the oxidation to sulfinyl, but usually taking an excess of them.

On the contrary, compounds of formula I, wherein Y is sulfinyl or sulfonyl, can be reduced to corresponding compounds of formula I wherein Y is sulfur. A suitable reduction means is for example catalytically activated hydrogen using nobel metals or their oxides as catalysts, such as palladium, platinum or rhodium or their oxides respectively, which are optionally distributed on a suitable carrier, such as charcoal or barium sulfate.

Furthermore, e.g. reducing metal cations, such as tin(II), lead(II), copper(I), manganese(II), titanium(II), vanadium(II), molybdenum(III) or tungsten(III) compounds; hydrogen halides, such as hydrogen chloride, bromide or iodide; hydrides, such as complex metal hydrides, for example lithium aluminium, sodiumboro or tributyltin hydride; phosphorous compounds, such as phosphorous halides, for example phosphorous trichloride or -tribromide, phosphorous pentachloride or -oxychloride; phosphines, such as triphenylphosphine; or phosphorous pentasulfide-pyridine; or sulfur compounds, such as mercaptanes, thioacids, thiophosphorous acids or dithiocarboxylic acids, dithionite or sulfur complexes, such as the iodine-pyridine-sulfur dioxide complex, can be used as reducing agents.

It is also possible in essentially the same manner as described above for compounds of formula I to convert in intermediate compounds, e.g. such formulae II and IV a sulfur group Y into sulfinyl or sulfonyl, a sulfinyl group Y into sulfonyl, or a sulfonyl or sulfinyl group Y into sulfur, provided that functional groups present which are sensitive to the above-described oxidation and reduction methods are protected by conventional protecting groups described below.

The conversions of compounds of formula I into other compounds of formula I described above for the radicals —B—(Z)$_n$ and Y as defined under formula I, can also be transferred to the preparation and modification of corresponding substituents within the whole molecule.

If any intermediates mentioned contain interfering reactive groups, e.g. carboxy, hydroxy, amino or mercapto groups, such may advantageously be temporarily protected at any stage with easily removable protecting groups. The choice of protecting groups for a particular reaction depends on several factors, e.g. the nature of the functional group to be protected, the structure and stability of the molecule of which the substituent is the functional group, and the reaction conditions. Protecting groups that meet these conditions and their introduction and removal are known to the art and are described, for example, in J. F. W. McOmie, "Protective Groups in Organic Chemistry", Plenum Press, London, New York 1973. Thus, carboxy groups are protected, for example, in esterified form, e.g. as unsubstituted or substituted lower alkyl esters, such as methyl or benzyl esters, it being possible for such ester groupings to be removed easily under mild conditions, especially alkaline conditions. Amino- and hydroxy-protecting groups that can be removed under mild conditions are for example acyl radicals, such as lower alkanoyl optionally substituted by halogen, e.g. formyl or trichloroacetyl, or organic silyl, e.g. tri-lower alkylsilyl, such as trimethylsilyl.

Depending upon the reaction conditions, the compounds of formula I are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. and alkali metal hydroxide or carbonate, or a cation exchange preparation. On the other hand, compounds of formula I containing acidic groups, e.g. carboxy or a phenolic hydroxy group, can be converted into salts in a manner known per se by treating with a base, e.g. an alkali metal hydroxide or alkoxide, an alkali metal or alkaline-earth metal salt, e.g. sodium hydrogen carbonate, ammonia or a suitable organic amine. The free compounds can be obtained by treating such salts with an acid. In view of the close relationship between the free compounds and the compounds in the form of their salts, whenever a compound is referred to in this context, a corresponding salt is also intended, provided such is possible or appropriate under the circumstances.

The compounds of formula I contain at least one asymmetric carbon atom, if the radicals $R_1$ and $R_2$ therein have different meanings. In that case they can be found as R- or S-enantiomers as well as enantiomeric mixtures thereof, such as a racemate. The present invention is intended to include all these forms, also those further isomers, and mixtures of at least two isomers, for example a diastereoisomeric mixture or enantiomeric mixture, which become possible if one or more further asymmetric center(s) are present within the molecule.

Any resulting mixtures of diastereoisomers, mixtures of racemates or geometric isomers can be separated on the basis of the physicochemical differences of the constituents, in known manner, into single diastereoisomers, racemates, or geometric isomers, for example by chromatography and/or fractional crystallisation.

Any resulting enantiomeric mixtures, such as racemics, can be resolved into the optical isomers (antipodes) by known methods, for example for recrystallisation from an optically active solvent, or with the aid of microorganisms, or by e.g. reacting an acidic end product with an optically active base that forms salts with the racemic acid, and separating the salts obtained in this manner, for example by fractional cyrstallization, into the diasteroisomeric salts from which the optically active carboxylic acid antipodes can be liberated on acidification. The basic racemic products can likewise be resolved into the optical antipodes, e.g. by separation of the diastereoisomeric salts thereof, with an optically active acid, and liberating the optically active basic compound by treatment with a standard base. Racemic products of the invention can thus be resolved into their optical antipodes, e.g., by fractional crystallization of d- or l-(tartrates, mandelates, camphorsulfonates), or of d- or l-(α-methylbenzylamine, cinchonidine, cinchonine, quinine, quinidine, ephedrine, dehydroabietylamine, brucine or strychnine) salts. Advantageously, the more active of the two antipodes is isolated.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, e.g. in a temperature range from $-20°$ to $+200°$ C., preferably at the boiling point of the solvents used, and at atmospheric or super-atmospheric pressure. The preferred solvents, catalysts and reaction conditions are set forth in the appended illustrative examples.

The compounds, including their salts, can also be obtained in the form of their hydrates, or include other solvents used for their crystallization.

The invention further includes any variant of the present processes, in which an intermediate product obtainable at any stage thereof is used as starting material and the remaining steps are carried out, or the process is discontinued at any stage thereof, or in which a starting material is formed under the reaction conditions, or in which a reaction component is used in the form of a salt or an optically pure antipode. Mainly those starting materials should be used in said reactions, that lead to the formation of those compounds indicated above as being especially useful. The invention also relates to novel starting materials and processes for their manufacture.

The pharmaceutical preparations according to the invention contain at least one compound of formula I or a pharmaceutically acceptable salt thereof as the active substance alone or together with customary carriers and adjuncts. They can be administered e.g. enterally, such as orally or rectally, parenterally, e.g. subcutaneously, intramuscularly or intravenously, or by inhalation. The daily doses for mammals of about 70 kg body weight, depending upon the type of disorder, individual condition, age and also on the mode of administration, are preferably between 10 mg and 10 g and especially between 50 mg and 3 g.

The novel pharmaceutical preparations contain preferably from about 0.1 to about 99%, especially from about 10 to about 90%, of the active substance. Pharmaceutical preparations according to the invention are e.g. those in dosage unit forms, such as tablets, dragees, capsules or suppositories, or those in the form of an aerosol or spray, and also ampoules.

The pharmaceutical preparations of the present invention are prepared in a manner known per se, for example by means of conventional mixing, granulating, dragee-making, dissolving or lyophilising processes. Thus, pharmaceutical preparations for oral use can be obtained by combining the active compound with solid carriers, granulating a resulting mixture if desired and processing the mixture or granules, after adding suitable adjuncts if desired or necessary, to give tablets or dragee cores.

Suitable carriers are, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragee cores may be provided with suitable coatings that may be resistant to gastric juices, there being used, inter alia, concentrated sugar solutions that may contain gum arabic, talc, polyvinylpyrrolidone, polyethylene glycol and/or titanium dioxide, or lacquer solutions in suitable organic solvents or solvent mixtures, or, for the manufacture of coatings resistant to gastric juices, solutions of suitable cellulose preparations, such as acetylcellulose phthalate or hydroxypropylmethylcellulose phthalate. Colourings or pigments may be added to the tablets or dragee coatings, for example for identification purposes or to indicate different doses of active ingredient.

Further orally administrable pharmaceutical preparations are dry-filled capsules consisting of gelatine, and also soft sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

There come into consideration as rectally administrable pharmaceutical preparations, for example, suppositories that consist of a combination of the active ingredient and a suppository base. Suitable as suppository bases are, for example, natural or synthetic triglycerides, paraffin hydrocarbons, polyethylene glycols or higher alkanols. It is also possible to use gelatine rectal capsules that contain a combination of the active ingredient and a base material; suitable base materials are, for example, liquid triglycerides, polyethylene glycols or paraffin hydrocarbons.

Suitable for parenteral administration are especially aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran and optionally stabilisers.

For inhalation the active compound may be presented in association with volatile excipients, as a cream, lotion, paste or ointment or as a finely divided dry powder or in solution for inhalation through a nasal spray, atomiser or insufflator.

Inhalation preparations for the treatment of the respiratory tract by nasal, buccal or intrapulmonary administration are e.g. aerosols or sprays that can disperse the pharmacological active ingredient in the form of a powder or in the form of drops of a solution or suspension. Preparations having powder-dispersing properties generally contain, apart from the active ingredient, a liquid propellent gas having a boiling point of below room temperature and, if desired, carriers, such as liquid or solid, non-ionic or anionic surface-active agents and/or solid diluents. Preparations in which the pharmacological active ingredient is in solution, contain, in addition, a suitable propellant, and also, if necessary, an additional solvent and/or a stabiliser. Instead of the propellent gas, it is also possible to use compressed air, and this can be produced as required by means of a suitable compression and release device.

The following Examples (a) to (f) are intended to illustrate the manufacture of some typical forms of administration, but do not in any way represent the only embodiments of those forms of administration.

(a) 250 g of active substance are mixed with 550 g of lactose and 292 g of potato starch, and the mixture is moistened with an alcoholic solution of 8 g of gelatine and granulated by being passed through a sieve. After drying, 60 g of talc, 10 g of magnesium stearate and 20 g of colloidal silica are added and the mixture is pressed to form 10,000 tablets each weighing 119 mg and each containing 25 mg of active substance, which may, if desired, be provided with dividing notches of a finer adjustment of the dosage.

(b) A granulate is prepared from 100 g of active substance, 379 g of lactose and the alcoholic solution of 6 g of gelatine, which, after being dried, is mixed with 10 g of colloidal silica, 40 g of talc, 60 g of potato starch and 5 g of magnesium stearate and pressed to form 10,000 dragee cores. These are subsequently coated with a concentrated syrup consisting of 533.5 g of cryst. saccharose, 20 g of shellac, 75 g of gum arabic, 250 g of talc, 20 g of colloidal silica and 1.5 g of colouring substance, and dried. The resulting dragees each weight 150 mg and each contain 10 mg of active substance.

(c) A sterile solution of 5.0 g of the active substance in 5000 ml of distilled water is introduced into 5 ml ampoules, the ampoules containing 5 mg of active ingredient in 5 ml of solution.

(d) 25 g of active substance and 1975 g of finely ground suppository base (for example, cocoa butter) are thoroughly mixed and then melted. 1000 suppositories of 2 g are cast from the melt which has been kept homogenous by stirring. They each contain 25 mg of active substance.

(e) 2000 mg of active substance—in a water-soluble form, e.g. as a salt—are dissolved in freshly distilled water with the addition of the equimolar amount of 2N sodium hydroxide solution. 10 mg of the stabiliser, e.g. ethylenediaminetetraacetic acid disodium salt, and 10 mg of the preservative, e.g. benzalkonium chloride, are then added. After all of the components have dissolved completely, the resulting solution is made up to 100 ml and filled into small bottles and these are sealed gas-tight.

(f) 25 g of active substance and 25 g of very finely ground lactose are intimately mixed. The resulting powder is then sieved and filled in 50 mg portions into 1,000 gelatine capsules.

The following examples are intended to illustrate the invention and are not to be construed as being limitations thereon. Temperatures are given in degrees Centigrade. If not mentioned otherwise, all evaporations are performed under reduced pressure, preferably between about 0.1 and 130 mbar.

EXAMPLE 1

To a stirred solution of 40.57 g 4-chloro-3-formylflav-3-ene in 150 ml dry pyridine is added 21.6 g ethyl thioglycolate. Subsequently one adds dropwise 21.2 g triethylamine while maintaining the reaction temperature below 10° C. After 2 h stirring at room temperature, and cooling to 0°-5° C., 30 ml 35% potassium hydroxide aqueous solution is added dropwise. After 30 min, the ethylester is precipitated by dilution with 1.5 l water and the suspension stirred 90 min at 3° C. The precipitate is filtered, washed with water and crystallized in hexane. Pure ethyl (4H-4-phenyl-thieno[3,2-c][1]benzopyran)-2-carboxylate is obtained as yellow crystals; m.p. 107°-108° C.

EXAMPLE 2

A solution containing 15 g 4-chloro-3-formyl-6-methylthioflav-3-ene, 7.3 ml ethyl thioglycolate and 66 ml pyridine is stirred at 7° C., when one adds 10.8 ml triethylamine. After 2 h stirring at 50° C. the solution is cooled to 3° C. and 11 ml of a 50% potassium hydroxide aqueous solution is added dropwise. After 15 min one adds 550 ml water and stirring is maintained for 2 h on an ice bath. The precipitate is dissolved in methylene chloride and this organic phase is washed with water to pH 7 dried and evaporated. The crude product is purified by column chromatography on silicagel using a mixture of n-hexane and methylene chloride as eluant. The best fractions are crystallized from a mixture of ethanol and water. Pure ethyl (4H-8-methyl-4-phenyl-thieno[3,2-c][1]benzothiopyran)-2-carboxylate is obtained; m.p. 108°-110° C.

EXAMPLE 3

As example 1, but starting from 31.9 g 4-chloro-6-fluoro-3-formyl-chrom-3-ene (m.p. 86° ). Pure ethyl (4H-8-fluorothieno-[3,2-c][1]benzopyran)-2-carboxylate is obtained; m.p. 108° C. The starting material is prepared by chloroformylation of the corresponding 4-chromanone (m.p. 114°-116°), which in turn is synthesized according to the procedure described in JACS 76, 5065 (1954).

EXAMPLE 4

As example 1, but starting from 45.9 g 4-chloro-2,2-dimethyl-6-fluoro-3-formyl-chrom-3-ene (m.p. 66°-69°). Pure ethyl (4H-4,4-dimethyl-8-fluoro-thieno[3,2-c][1]benzopyran)-2-carboxylate is obtained; m.p. 121°-122° C. The starting material is prepared by chloroformylation of the corresponding 4-chromanone (m.p. 32°-37°), which in turn is synthesized according to the procedure described in Synthesis 1978, 886.

EXAMPLE 5

As example 1, but starting from 36.1 g 4-chloro-3-formyl-8-methoxy-thiochrom-3-ene (m.p. 99.5°-100.5°). Pure ethyl (4H-6-methoxy-thieno-[3,2-c][1]benzothiopyran)-2-carboxylate is obtained; m.p. 66° C. The starting material is prepared by chloroformylation of the corresponding 4-thiochromanone (m.p. 106°-108°), which in turn is synthesized according to the procedure described in JACS 76, 5065 (1954).

EXAMPLE 6

As example 1, but starting from 31.6 g 4-chloro-6-fluoro-3-formyl-1,2-dihydronaphthalene (m.p. 53°-54°). Pure ethyl (4,5-dihydro-8-fluoro-naphtho[1,2-b]thiophene)-2-carboxylate is obtained; m.p. 78°–79° C. The starting material is prepared by chloroformylation of the corresponding 1-tetralone (m.p. 63.5°–65°) described in JACS 89, 386 (1967).

EXAMPLE 7

As example 1, but starting from 28.8 g 3-chloro-4-formyl-1,2-dihydronaphthalene. The ethyl ester is not precipitated by dilution with 1.5 l water but is extracted from the mixture with diethylether. Pure ethyl (4,5-dihydronaphtho[2,1-b]thiophene)-2-carboxylate is obtained as an oil after drying and solvent evaporation.

EXAMPLE 8

A solution of 33.6 g ethyl (4H-4-phenyl-thieno[3,2-c][1]benzopyran)-2-carboxylate and 20 g potassium hydroxide in 1 liter ethanol is refluxed for 1 h. The reaction mixture is evaporated to dryness and the residue dissolved in 600 ml water. The solution is acidified with 235 ml 5% hydrochloric acid aqueous solution; the formed precipitate is filtered, washed with water and dried. This solid is crystallized in 98% ethanol and pure 4H-4-phenyl-thieno[3,2-c][1]benzopyran-2-carboxylic acid is obtained; m.p. 258°–260° C.

The sodium salt of this carboxylic acid is prepared by treating the stirred suspension of the acid in hot water (90°–100° C.) with 1 equivalent sodium hydroxide aqueous solution. After extraction with chloroform, the clear aqueous solution is evaporated in vacuo. The residue is dried over potassium hydroxide in vacuo. Water contents of the salt are determined by $^1$H-NMR spectroscopy in dimethylsulfoxide and by microanalysis; m.p. 215° C. (decomposition).

Microanalysis: Found C 63.55; H 3.59; S 9.53; Na 6.76.
Calc. for $C_{18}H_{13}NaO_4S.0.5H_2O$ C 63.71; h 3.56; S 9.44; Na 6.77.

EXAMPLE 9

A solution of 15 g ethyl (4H-8-methyl-4-phenyl-thieno[3,2-c][1]benzothiopyran)-2-carboxylate and 8.9 g sodium hydroxide in 382 ml ethanol is refluxed for one hour and evaporated. The residue is dissolved in water and this aqueous phase is washed with methylene chloride. Acidification with a 37% hydrochloric acid solution leads to precipitation of a product which is crystallized from a mixture of n-hexane and toluene. Pure 4H-8-methyl-4-phenylthieno[3,2-c][1]benzothiopyran-2-carboxylic acid is obtained as yellow crystals; m.p. 205°–209°. Sodium salt (prepared as described in example 8): m.p. 195° C. (decomposition).
Microanalysis: Found: C 59.82; H 4.07; S 16.81; Na 6.03. Calc. for $C_{19}H_{13}NaO_2S_2.1.17H_2O$: C 59.76; H 4.09; S 16.58; Na 5.88.

EXAMPLE 10

As example 8, but starting from 27.8 g ethyl (4H-8-fluoro-thieno[3,2-c][1]benzopyran)-2-carboxylate. Pure 4H-8-fluoro-thieno[3,2-c][1]-benzopyran-2-carboxylic acid is obtained; m.p. 260° (decomposition).
Sodium salt microanalysis: Found: C 46.74; H 3.34; S 10.37; F. 5.95. Calc. for $C_{12}H_6O_3SFNa.2H_2O$: C 46.76; H 3.27; S 10.40; F 6.16.

EXAMPLE 11

As example 8, but starting from 30.6 g ethyl (4H-4,4-dimethyl-8-fluoro-thieno[3,2-c][19 benzopyran)-2-carboxylate. Pure 4H-4,4-dimethyl-8-fluoro-thieno[3,2-c][1]benzopyran-2-carboxylic acid is obtained; m.p. 234°–238° C.
Sodium salt microanalysis: Found: C 53.84; H 3.74; S 10.33; F 6.03. Calc. for $C_{14}H_{10}O_3SFNa.0.73H_2O$: C 53.65; H 3.69; S 10.23; F 6.06.

EXAMPLE 12

As example 8, but starting from 34.6 g ethyl (4H-8-fluoro-4-spirocyclohexyl-thieno[3,2-c][1]benzopyran)-2-carboxylate. Pure 4H-8-fluoro-4-spirocyclohexyl-thieno[3,2-c][1]benzopyran-2-carboxylic acid is obtained; m.p. 234°–238° C.
Sodium salt microanalysis:
Found: C 56.95; H 4.51; S 9.00; F 5.14. Calc. for $C_{17}H_{14}O_3SFNa.1 H_2O$: C 56.98; H 4.50; S 8.95; F 5.30.
The starting material can be obtained by reacting 4-chloro-6-fluoro-3-formyl-2-spirocyclohexyl-chrom-3-ene (m.p. 77°–80°) with ethyl thioglycolate analogous to the procedure described in example 1. The chloroformyl compound just mentioned is prepared by chloroformylation of the corresponding 4-chromanone [$^1$H-NMR: δ=1.1–2.2 (10H, m); 2.75 (2H, s); 6.9–7.7 (3H, m)], which in turn is synthesized according to the procedure described in Synthesis 1978, 886.

EXAMPLE 13

As example 8, but starting from 30.6 g ethyl (4H-6-methoxy-thieno[3,2-c][1]benzothiopyran)-2-carboxylate. Pure 4H-6-methoxy-thieno[3,2-c[]1]benzothiopyran-2-carboxylic acid is obtained; m.p. 260° C.
Sodium salt microanalysis: Found: C 47.18; H 3.63; S 19.25. Calc. for $C_{13}H_9O_3S_2Na.1.7 H_2O$: C 47.18; H 3.78; S 19.37.

EXAMPLE 14

As example 8, but starting from 27.6 g ethyl (4,5-dihydro-8-fluoro-naphtho[1,2-b]thiophene)-2-carboxylate. Pure 4,5-dihydro-8-fluoro-naptho[1,2-b]thiophene-2-carboxylic acid is obtained; m.p. 240°–242° C.
Sodium salt microanalysis: Found: C 54.34; H 3.46; Na 8.13. Calc. for $C_{13}H_8O_2SFNa.0.9 H_2O$: C 54.50; H 3.45; Na 8.03.

EXAMPLE 15

As example 8, but starting from 25.8 g ethyl (4,5-dihydro-naphtho[2,1-b]thiophene)-2-carboxylate. Pure 4,5-dihydronaphtho[2,1-b]thiophene-2-carboxylic acid is obtained; m.p. 205°–208° C.
Sodium salt microanalysis: Found: C 58.50; H 4.02; S 12.04. Calc. for $C_{13}H_9O_2SNa.0.8 H_2O$: C 58.55; H 4.02; S 12.02.

EXAMPLE 16

To a stirred solution of 21 g 4-chloro-3-formyl-thiochrom-3-ene in 80 ml dry dimethylsulfoxide under nitrogen is added 15 g mercaptosuccinic acid. 36 ml triethylamine is then added dropwise and subsequently the reaction mixture is kept at 90°–100° C. for 30 minutes. The mixture is then diluted with water, acidified with hydrochloric acid and extracted with diethylether. The organic layer is then extracted with aqueous sodium bicarbonate solution. After acidification of the aqueous layer the product precipitates as a tar. It is taken up in chloroform. After evaporation of the solvent the residue is recrystallized from a mixture of chloroform and cyclohexane. Pure (4H-thieno[3,2-c][1]benzothiopyran-2-yl)acetic acid is obtained; m.p. 106°–110° C.

Sodium salt microanalysis (formed as in example 8): Found: C 54.26; H 3.35; S 22.29. Calc. for $C_{13}H_9O_2S_2\cdot Na\cdot 0.2H_2O$: C 54.23; H 3.29; S 22.27.

EXAMPLE 17

As example 16, but starting from 19.3 g 4-chloro-3-formyl-1,2-dihydro-naphthalene. Pure (4,5-dihydronaphtho[1,2-b]thiophene-2-yl)acetic acid is obtained; m.p. 103°–105° C.

Sodium salt microanalysis (prepared as described in example 8): Found: C 62.72; H 4.30; S 11.60. Calc. for $C_{14}H_{11}O_2SNa\cdot 0.1H_2O$: C 62.72; H 4.21; S 11.96.

EXAMPLE 18

As example 16 but starting from 17 g 4-chloro-3-formyl-2-phenyl-chrom-3-ene. Pure (4H-4-phenyl-thieno[3,2-c][1]benzopyran-2-yl)acetic acid is obtained after recrystallization in a mixture of methanol and water; m.p. 105°–110° C.

Sodium salt microanalysis (prepared as described in example 8): Found: C 62.67; H 4.35; S 8.70. Calc. for $C_{19}H_{13}SO_3Na\cdot 1H_2O$: C 62.97; H 4.17; S 8.84.

EXAMPLE 19

9.8 ml triethylamine is added dropwise to a stirred, cooled (10° C.) solution of 13.5 g 4-chloro-3-formyl-2-phenyl-chrom-3-ene and 12.3 g freshly distilled 2-ethylhexyl thioglycolate in 60 ml pyridine. Stirring at room temperature is continued for 2 h. Subsequently the mixture is cooled (3°–5° C.) and 10.1 ml 50% aqueous potassium hydroxide is slowly added. After 30 min, the mixture is diluted with 800 ml water, allowed to stir at 20° for 2 h, and extracted with diethylether. The etheral extracts are washed with water, 2N hydrochloric acid solution, water then dried and evaporated. The residue is purified by column chromatography over silicagel with chloroform. Pure colorless oily 2-ethylhexyl (4H-4-phenyl-thieno[3,2-c][1]benzopyran)-2-carboxylate is obtained; TLC (SiO$_2$), CHCl$_3$/CCl$_4$ 1:1): Rf=0.63.

EXAMPLE 20

A stirred solution of 17.6 g 4H-4-phenyl-thieno[3,2-c][1]benzopyran-2-carboxaldehyde, 12.5 g malonic acid and 24 ml pyridine is slightly heated until a clear solution is obtained. Subsequently, 1 ml piperidine is added and the solution slowly heated to reflux. After 3 h reflux, the solution is cooled and poured into water. After acidification with hydrochloric acid, the crude product is filtered off, dried, recrystallized from ethyl acetate and dried in vacuo. Pure 3-(4H-4-phenyl-thieno[3,2-c][1]benzopyran-2yl)propenoic acid is obtained; m.p. 235° C. (decomposition).

Microanalysis: Found: C 71.88; H 4.28; O 14.46; S 9.59. Calc. for $C_{20}H_{14}SO_3$: C 71.84; H 4.22; O 14.35; S 9.19.

The sodium salt is prepared by treatment of a solution of 5 g of the carboxylic acid in 300 ml acetone with one equivalent 1N sodium hydroxide. The solvent is evaporated and the residue recrystallized from water. This salt is slightly light-sensitive.

EXAMPLE 21

To a suspension of 4.2 g 4-chloro-3-formyl-flav-3-ene in 10 ml pyridine is added a solution of 2.6 g 2,5-dihydroxy-1,4-dithian and 2.2 g triethylamine in 11 ml pyridine. After overnight stirring one adds slowly 100 ml water and the precipitate is collected, washed with water, dried, and crystallized in absolute ethanol. Pure 4H-4-phenyl-thieno[3,2-c][1]benzopyran-2-carboxaldehyde is obtained; m.p. 117°–118° C.

EXAMPLE 22

As example 21, but starting from 4.7 g 4-chloro-3-formyl-6-methyl-thioflav-3-ene. Pure 4H-8-methyl-4-phenyl-thieno[3,2-c][1]benzothiopyran-2-carboxaldehyde is obtained as yellow crystals after recrystallization in a mixture of n-hexane and acetone; m.p. 106°.

EXAMPLE 23

A solution of 43.8 g 4H-4-phenyl-thieno[3,2-c][1]benzopyran-2-carboxaldehyde in 250 ml pyridine is stirred at room temperature. To this solution 20.85 g hydroxylamine hydrochloride is added. After stirring 1 h at 80° and evaporation, the resulting solid is dissolved in methylene chloride, washed with a 2N hydrochlorid acid solution, then with water, dried and evaporated. The residue is purified by high pressure liquid chromatography on silicagel using a mixture of n-hexane and methylene chloride as eluant. The best fractions give pure 4H-4-phenyl-thieno[3,2-c][1]benzopyran-2-carboxyaldehyde-(E)-oxime; m.p. 164°–167° C.

EXAMPLE 24

As example 23, but besides product described in example 23, one can collect a second set of fractions which corresponds to pure 4H-4-phenyl-thieno[3,2-c][1]benzopyran-2-carboxaldehyde-(Z)-oxime as a yellow powder; m.p. 153°–156° C.

EXAMPLE 24

To a suspension of 2.9 g 4H-4-phenyl-thieno[3,2-c][1]benzopyran-2-carboxaldehyde in 30 ml absolute methanol is added 0.79 g sodium borohydride. After hydrolysis with 10 ml water, the methanol is evaporated and the product extracted with methylene chloride. The residual solid is crystallised in a mixture of ethyl acetate and ligroin. Pure off-white 4H-2-hydroxymethyl-4-phenyl-thieno[3,2-c][1]benzopyran is obtained; m.p. 100°–101° C.

EXAMPLE 26

A suspension of 5.9 g 4H-2-hydroxymethyl-4-phenyl-thieno[3,2-c][1]benzopyran and 5.8 g of palmitoyl chloride in 50 ml pyridine is stirred at room temperature for 4 h. After filtration, one adds 400 ml water to the filtrate. The precipitate which appears is collected. This material is dissolved in methylene chloride and this organic phase is washed with hydrochloric acid solution, then with water, dried and evaporated. The residue is purified by column chromatography on silicagel using a mixture of n-hexane and methylene chloride as eluant. Pure 4H-2-palmitoyloxymethyl-4-phenyl-thieno[3,2-c][1]benzopyran is obtained as a white powder; m.p. 64°–65° C.

EXAMPLE 27

A suspension of 12.5 g phosphorous pentachloride in 30 ml anhydrous tetrahydrofuran is stirred at room temperature. A solution of 15.4 g 4H-4-phenyl-thieno[3,2-c][1]benzopyran-2-carboxaldehyde-(Z)-oxime in 100 ml anhydrous tetrahydrofuran is added dropwise and stirring is maintained for 1.5 h. The reaction mixture is poured into 100 g crushed ice and neutralized with 250 ml saturated sodium bicarbonate solution. Tetrahydrofuran is evaporated and the aqueous phase extracted with methylene chloride. The organic phase is washed with water and dried over magnesium sulfate. The solid residue is crystallized in ethanol. 4H-2-cyano-4-phenyl-thieno[3,2-c][1]benzopyran is obtained as orange-coloured crystals; m.p. 138°–140° C.

EXAMPLE 28

To a stirred suspension of 1.57 g lithium aluminium hydride in 30 ml tetrahydrofuran at room temperature is added dropwise a solution of 7.96 g 4H-2-cyano-4-phenyl-thieno[3,2-c][1]benzopyran in 50 ml tetrahydrofuran. After 2 h stirring, the reaction mixture is allowed to 0° C. Hydrolysis with 6.6 ml water and 1.6 ml 15% sodium hydroxde solution is followed by filtration. The filtrate is evaporated under vacuo and the residue dissolved in methylene chloride. This solution is acidified with 50 ml 1N hydrochloric acid solution. A precipitate forms which is filtered, washed with methylene chloride, dried and crystallized in water. Pure 4H-2-aminomethyl-4-phenyl-thieno[3,2-c][1]benzopyran hydrochloride is obtained; m.p. 224°–225° C.

EXAMPLE 29

10 g of ethyl (4H-4-phenyl-thieno[3,2-c][1]benzopyran)-2-carboxylate is added to a stirred solution of 0.1 g sodium in 500 ml absolute methanol. A slow stream of ammonia is bubbled through the reaction mixture at room temperature for one week. After evaporation of the methanol the residue is taken up with water, filtered, washed with water to pH 7 and dried. Pure 4H-2-carboxamido-4-phenyl-thieno[3,2-c][1]benzopyran is obtained as a pale yellow powder; m.p. 228°–230° C.

EXAMPLE 30

20.3 g 2-mercaptoacetamide is dissolved into a basic solution of 9.8 g sodium hydroxide in 180 ml methanol. This solution is slowly added to a suspension of 55 g 4-chloro-3-formyl-flav-3-ene in 350 ml methanol. After 4 h stirring at room temperature, the reaction is cooled down to 3° C. and the precipitate is filtered, washed with water and the crude product recrystallized in dioxane. Pure 4H-2-carboxamido-4-phenyl-thieno[3,2-c][1]benzopyran is obtained as a pale yellow crystals; m.p. 228°–230° C.

EXAMPLE 31

A mixture of 8.68 g 4H-2-cyano-4-phenyl-thieno[3,2-c][1]benzopyran, 2.15 g sodium azide, 1.77 g ammonium chloride and 90 ml N,N-dimethylformamide is heated and stirred at 80° under nitrogen for 20 hours. The reaction mixture is filtered, and the N,N-dimethylformamide evaporated. The residue is dissolved in 150 ml of a 1N sodium hydroxide aqueous solution which is then washed with methylene chloride. The aqueous phase is acidified with 200 ml of 1N hydrochloric acid solution and the precipitate which forms is filtered, washed with water and dried. Pure 4H-2-(1H-tetrazol-1,2,3,4-5-yl)-4-phenyl-thieno[3,2-c][1]benzopyran is obtained as a beige powder. TLC (SiO$_2$, methylene chloride/acetone/formic acid 18:1:1), single spot, R$_f$=0,51.-
$^1$H-NMR (100 MHz, DMSO-d$_6$):

δ(ppm)=6,2 (1H, s): 6.8–7.6 (9H, m): 7.04 (1H, s); 7.8–8.6 (1H, s, NH).

Microanalysis: Found: C 65.26; H 3.89; N 16.64; O 4.88; S 9.37. C$_{18}$H$_{12}$N$_4$OS Calc.: C 65.05; H 3.64; N 16.86; O 4.82; S 9.65.

EXAMPLE 32

A suspension of 4.65 g 4H-2-(1H-tetrazol-1,2,3,4-5-yl)-4-phenyl-thieno[3,2-c][1]benzopyran in 20 ml absolute methanol is stirred at room temperature under nitrogen. A solution of 0.32 g sodium in 20 ml absolute methanol is added dropwise. After complete disappearance of the substrate, the solvent is evaporated. The residual solid is crystallized in water, and pure 4H-2-(sodium-1H-tetrazolate-1,2,3,4-5-yl)-4-phenyl-thieno[3,2-c][1]benzopyran is obtained.
$^1$H-NMR (DMSO-d$_6$): δ(ppm)=6.58 (1H, s); 6.8–7.6 (9H, m); 7.06 (1H, s); absence of N—H.

EXAMPLE 33

A suspension of 10 g ethyl (4H-4-phenyl-thieno[3,2-c][1]benzopyran)-2-carboxylate in 100 ml absolute ethanol is stirred under nitrogen at room temperature. One adds 10 g hydrazine hydrate. After refluxing the mixture for 45 h, the solution is allowed to cool. The precipitate is filtered, washed with ethanol and dried. Pure 4H-2-hydrazinocarbonyl-4-phenyl-thieno[3,2-c][1]benzopyran is obtained; m.p. 238°–239°.

EXAMPLE 34

A solution of 8.29 g 4H-4-phenyl-thieno[3,2-c][1]benzopyran-2-carboxaldehyde-(E)-oxime in 50 ml pyridine is cooled at 0° C. To this solution, 4.4 g of acetyl chloride is added and stirring is maintained while the temperature is allowed to rise to 20°. The reaction mixture is evaporated under reduced pressure. The residue is dissolved in methylene chloride, washed with a 1% hydrochloric acid aqueous solution, then with water to pH 7, dried over magnesium sulfate and evaporated. The resulting solid is crystallized in ethyl acetate. Pure 4H-4-phenyl-thieno[3,2-c][1]benzopyran-2-carboxaldehyde-(E)-N-acetyl oxime is obtained as yellow crystals; m.p. 170°–171° C.

EXAMPLE 35

A suspension of 10.2 g 4-(N-methylcarboxamide-methylthio)-2-phenyl-2H-1-benzopyran-3-carboxaldehyde in a solution of 1.5 g NaOH in 40 methanol is stirred at 20° for 30 min, then filtered, washed with water and dried. Pure powdered N-methyl-4H-2-carboxamido-4-phenyl-thieno[3,2-c][1]benzopyran is obtained; m.p. 241°–242°.

The starting material is prepared as follows:

A solution of 3.8 g NaOH and 8.5 ml N-methylmercaptoacetamide in 80 ml methanol is slowly added to a cooled solution of 20 g 4-chloro-2-phenyl-2H-1-benzopyran-3-carboxaldehyde in 120 ml methanol. After 15 min stirring, one adds 100 ml water and the reaction mixture is evaporated. Extraction with methylene chloride, washing of the organic phase with water, drying and evaporation yields a crude product which is purified by preparative HPLC (SiO$_2$; CH$_2$Cl$_2$/acetone 9:1). Pure 4-(N-methylcarboxamido-methylthio)-2-phenyl-2H-1-benzopyran-3-carboxaldehyde is obtained; m.p. 132°–134°.

EXAMPLE 36

A mixture of 0.66 g sodium (4H-4-phenyl-thieno[3,2-c][1]benzopyran)-2-carboxylate, 0.36 ml benzyl chloride and 5 ml N,N-dimethylformamide is stirred for 20 h at 70°, then filtered and evaporated. The residue is crystallized in a mixture of ethyl acetate and methanol to yield pure benzyl (4H-4-phenyl-thieno[3,2-c][1]benzopyran)-2-carboxylate as pale yellow crystals; m.p. 138.5°–140°.

EXAMPLE 37

As example 36, but using 0.48 g 4-chlorobenzyl chloride, yields pure 4-chlorobenzyl (4H-4-phenyl-thieno[3,2-c][1]benzopyran)-2-carboxylate; m.p. 137.5°–139°.

EXAMPLE 38

0.5 ml thionyl chloride is added to a suspension of 1 g 4H-4-phenyl-thieno[3,2-c][1]benzopyran-2-carboxylic acid in 20 ml methylene chloride. After 2 h reflux and evaporation, the crude acid chloride is solved in 20 ml methylene chloride; this solution is stirred vigorously at 20° with a 5 ml aqueous solution of 0.3 g sodium azide and 4 mg tetrabutyl ammonium chloride. After 75 min, the organic phase is washed with water, dried, and refluxed for one week with 1.5 ml trifluoroacetic acid, then neutralized, washed with water, dried and evaporated. The crude product is purified by filtration over silicagel to yield pure 4H-4-phenyl-2-trifluoroacetylamino-thieno[3,2-c][1]benzopyran; m.p. 174°–176,5°.

EXAMPLE 39

456 mg 4,5-dihydro-naphtho[1,2-b]thiophene-2-carboxylic acid [e.g. DE-A-1,953,809] is treated with 5 ml thionylchloride, heated and stirred for 2 h. The excess thionylchloride is evaporated and the crude product is dried. The acid chloride is dissolved in 5 ml methylene chloride and cooled down to 0°. To this solution is slowly added 5 ml concentrated ammonia solution. After 2 h stirring and evaporation, the resulting solid is dissolved in methylene chloride, washed with water, dried and evaporated. The residual solid is purified by washing in diisopropylether and recrystallized in methylene chloride. Pure 4,5-dihydro-2-carboxamido-naphtho[1,2-b]thiophene is obtained as a white powder; m.p. 117°–119°.

EXAMPLE 40

As example 39, but starting from 465 mg 4H-4,4-dimethyl-8-fluoro-thieno[3,2-c][1]benzopyran-2-carboxylic acid. Pure 4H-2-carboxamido-4,4-dimethyl-8-fluoro-thieno[3,2-c][1]benzopyran is obtained as a white powder after recrystallization in methylene chloride; m.p. 199°–200°.

EXAMPLE 41

As example 39, but starting from 470 mg 4H-8-fluoro-4-spirocyclohexyl-thieno[3,2-c][1]benzopyran-2-carboxylic acid. Pure 4H-2-carboxamido-8-fluoro-4-spirocyclohexyl-thieno[3,2-c][1]benzopyran is obtained as a beige powder after recrystallization in methylene chloride; m.p. 276°–278°.

EXAMPLE 42

51.4 mg 2-mercaptoacetamide is dissolved in a basic solution of 24.6 mg sodium hydroxide in 0.45 ml methanol. This solution is slowly added to a suspension of 100 ml 4-chloro-3-formyl-chrom-3-ene in 0.5 ml methanol. After 16 h stirring at room temperature, the reaction is cooled down to 3°, then 4 ml water is added and the precipitate is filtered, washed with water and the crude product recrystallized in a mixture of 1,2-dimethoxyethan and cyclohexane. Pure 4H-2-carboxamido-thieno[3,2-c][1]benzopyran is obtained as white crystals; m.p. 166°–168°.

EXAMPLE 43

As example 42, but starting from 100 mg 4-chloro-6-fluoro-3-formyl-1,2-dihydro-naphthalene. Pure 4,5-dihydro-8-fluoro-2-carboxamide-naphtho[1,2-b]thiophene is obtained as white crystals after purification by column chromatography [SiO$_2$; n-hexane/acetone); m.p. 151°–153°.

EXAMPLE 44

As example 42, but starting from 100 mg 4-chloro-3-formyl-thiochrom-3-ene. Pure 4H-2-carboxamido-thieno[3,2-c][1]benzothipyran is obtained as white crystals after recrystallization in a mixture of 1,2-dimethoxyethan and cyclohexane; m.p. 161°–163°.

EXAMPLE 45

As example 42, but starting from 100 mg 4-chloro-3-formyl-6-methyl-thioflav-3-ene. Pure 4H-2-carboxamido-8-methyl-4-phenyl-thieno[3,2-c][1]benzothiopyran is obtained as white crystals after recrystallization in a mixture of 1,2-dimethoxyethan and cyclohexane; m.p. 208°–210°.

EXAMPLE 46

As example 42, but starting from 100 mg 4-chloro-3-formyl-4'-hydroxy-flav-3-ene. Pure 4H-2-carboxamido-4-(4-hydroxyphenyl)-thieno[3,2-c][1]benzopyran is obtained as pale pink white crystals after recrystallization in a mixture of methanol and acetone; m.p. 228°–230°.

EXAMPLE 47

As example 42, but starting from 100 mg 4-chloro-3-formyl-5-hydroxy-flav-3-ene. Pure 4H-2carboxamido-9-hydroxy-4-phenyl-thieno[3,2-c][1]benzopyran is obtained as white crystals after recrystallization in a mixture of methanol and acetone; m.p. 259°–262°.

EXAMPLE 48

As example 42, but starting from 100 mg 4-chloro-3-formyl-thioflav-3-ene. Pure 4H-2-carboxamide-4-phenyl-thieno[3,2-c][1]benzothiopyran is obtained as white crystals after recrystallization in a mixture of acetone and water; m.p. 190°–191°.

EXAMPLE 49

As example 42, but starting from 100 mg 4-chloro-3-formyl-8-methoxy-thiochrom-3-ene. Pure 4H-2-carboxamido-6-methoxy-thieno[3,2-c][1]benzothiopyran is obtained as pale yellow crystals after recrystallization in a mixture of 1,2-dimethoxyethan and cyclohexane; m.p. 205°–209°.

EXAMPLE 50

As example 42, but starting from 100 mg 4-chloro-6-fluoro-3-formyl-chrom-3-ene. Pure 4H-2-carboxamido-8-fluoro-thieno[3,2-c][1]benzopyran is obtained as white crystals after recrystallization in 1,2-dimethoxyethan; m.p. 180°–182°.

EXAMPLE 51

As example 42, but starting from 100 mg 4-chloro-3-formyl-1-methyl-1,2-dihydro-naphthalene. Pure 4,5-dihydro-5-methyl-2-carboxamido-naphtho[1,2-b]thiophene is obtained as white crystals after purification by column chromatograph (SiO₂; n-hexane/acetone); m.p. 167°–169°.

EXAMPLE 52

A solution of 300 mg ethyl (4H-8-methyl-4-phenyl-thieno[3,2-c][1]benzothiopyran)-2-carboxylate in 3 ml dichloromethane is treated at 0° with 173 mg 3-chloro-perbenzoic acid. After 5 min, the solution is hydrolysed with sodium bicarbonate solution, washed with sodium thiosulfate aqueous solution, then with water. After evaporation, the crude product is purified by column chromatography [SiO₂; n-hexane/ethyl acetate 2:1]. Pure ethyl (4H-8-methyl-4-phenyl-thieno[3,2-c][1]benzothiopyran-5-oxide)-2-carboxylate is obtained as a white powder; m.p. 150.5°–153°.

EXAMPLE 53

As example 52, but using 346 mg 3-chloro-perbenzoic acid at 20°. Pure ethyl (4H-8-methyl-4-phenyl-thieno[3,2-c][1]benzothiopyran-5,5-dioxide)-2-carboxylate is obtained without column chromatography as a white powder; m.p. 185°–188°.

EXAMPLE 54

(+)-sodium 4H-4-phenyl-thieno[3,2-c][1]benzopyran-2-carboxylate, $[\alpha]_{436}^{25} = +89°$ (c=0.5, methanol), is prepared according to examples 1 and 8 in the same manner as the corresponding racemate, but starting from the pure enantiomeric 4-chloro-3-formyl-flav-3-ene which is obtained by chloroformylation of (+)-flavonone [(+) at 436 nm] as e.g. described in example 1 of EP-A-139615.

Analogously, (−)-sodium 4H-4-phenyl-thieno[3,2-c][1]benzopyran-2-carboxylate, $[\alpha]_{436}^{25} = -89°$ (c=0.5, methanol), is prepared starting from the pure enantiomeric 4-chloro-3-formyl-flav-3-ene which is obtained by chloroformylation of (−)-flavanone [(−) at 436 nm]. The preparation of (+)- and (−)-flavanone is described e.g. in Tetrahedron Lett. 26, 2305 (1970) and Acta Chim. Acad. Sci. Hung. 86, 161 (1975).

EXAMPLE 55

(+)-4H-2-carboxamido-4-phenyl-thieno[3,2-c][1]benzopyran, $[\alpha]_{436}^{25} = +110°$ (c=0.5, acetone), is prepared according to example 30 in the same manner as the corresponding racemate, but starting from the pure enantiometric 4-chloro-3-formyl-flav-3-ene which is obtained by chloroformylation of (+)-flavanone [(+) at 436 nm] according to EP-A-139615.

Analogously, (−)-4H-2-carboxamido-4-phenyl-thieno[3,2-c][1]benzopyran, $[\alpha]_{436}^{25} = -110°$ (c=0.5, acetone) is prepared starting from the pure enantiomeric 4-chloro-3-formyl-flav-3-ene which is obtained by chloroformylation of (−)-flavanone [(−) at 436 nm].

I claim:

1. A compound of the formula

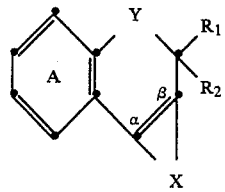

(I)

wherein ring A is unsubstituted or substituted by 1 or 2 substituents selected from the group consisting of lower alkyl, hydroxy, lower alkoxy, lower alkylenedioxy, lower alkanoyloxy, halogen, lower alkylamino, di-lower alkylamino, lower alkanoylamino, lower alkanoyl, carboxy and lower alkoxycarbonyl, $R_1$ and $R_2$, independently of one another, each represents hydrogen, lower alkyl or phenyl which is unsubstituted or substituted in the same manner as indicated above for the ring A, Y is methylene, oxygen or sulfur, X represents a bivalent radical —S—C(—B—(Z)ₙ)=CH— the sulfur group S of which is bound directly to the alpha- or to the β-position of the bicyclic ring system, B denotes a direct bond, lower alkylene or lower alkenylene, n is 1 or, in the case where B is lower alkylene or lower alkenylene, may also be 2 or 3, and Z represents carboxy, alkoxycarbonyl, carbamoyl which is unsubstituted or substituted by one or two equal or different radicals selected from the group consisting of (a) lower alkyl; (b) phenyl-lower alkyl, the phenyl group in turn being unsubstituted or substituted in the same manner as indicated above for the ring A; (c) amino; (d) lower alkylamino; and (e) di-lower alkylamino; esterified or amidated carboxy that can be cleaved under physiological conditions selected from lower alkanoyloxymethoxycarbonyl, amino-lower alkanoyloxymethoxycarbonyl, lower alkanoylamino-methoxycarbonyl, 3-phthalidyloxycarbonyl, 1-lower alkoxycarbonyloxy-lower alkoxycarbonyl, 1-lower alkoxy-lower alkoxycarbonyl, 2-oxo-1,3-dioxolen-4-yl methoxycarbonyl that is unsubstituted or substituted by lower alkyl or phenyl in the 5-position of the dioxolene ring, and carboxymethylcarbamoyl; cyano, hydroxycarbamoyl, 5-tetrazolyl, unsubstituted or lower alkyl-substituted 4,5-dihydro-2-oxazolyl, formyl, iminomethyl which is unsubstituted or substituted by hydroxy, lower alkoxy, or lower alkanoyloxy, or lower alkanoyl which is unsubstituted or substituted by halogen, or benzoyl or phenyl-lower alkanoyl each of which is unsubstituted or substituted in the phenyl ring as indicated above for the ring A, sulfo, lower alkoxysulfonyl, sulfamoyl, lower alkylsulfamoyl, di-lower alkylsulfamoyl, hydroxy, lower alkoxy, alkanoyloxy, amino, lower alkylamino, di-lower alkylamino, lower alkyleneamino, N-morpholino, N-thiomorpholino, N-piperazino which is unsubstituted or substituted by lower alkyl at its 4-position nitrogen atom, lower alkanoylamino, halo-lower alkanoylamino, nitro or halogen; with the provisos (a) that $R_1$ is phenyl unsubstituted or substituted as defined above, if $R_2$ represents hydrogen, Y denotes methylene and X is (alpha)—S—C(—Z)=CH—(β) wherein Z denotes carboxy or said esterified or amidated carboxy as defined above, (b) that ring A is substituted as defined above, if $R_1$ and $R_2$ both are hydrogen Y represents oxygen or sulfur and X is (alpha)—S—C(—COOH)=CH—(β), and (c) that Y is oxygen or sulfur, if $R_1$ and $R_2$ both are hydrogen, X is (alpha)—S—C(—Z)=CH—(β) wherein Z denotes carboxy, ethoxycarbonyl, cyano, formyl, acetyl, nitro or bromo, and ring A is unsubstituted or monosubstituted in 7-position by methoxy or acetyl;

or a tautomer, a stereoisomer or an optical isomer thereof, or a mixture of optical isomers; or a pharmaceutically acceptable salt thereof.

2. The compound of claim 1, wherein ring A is unsubstituted or monosubstituted by lower alkyl, hydroxy, lower alkoxy or halogen, $R_1$ and $R_2$, independently of one another, each represents hydrogen, lower alkyl or phenyl which phenyl is unsubstituted or monosubstituted in the same manner as indicated for the ring A, Y is methylene, oxygen, or sulfur, X represents a bivalent radical —S—C(—B—(Z)$_n$)=CH— the sulfur group S of which is bound directly to the alpha- or to the β-position of the bicyclic ring system, B denotes a direct bond, (C$_1$-C$_4$)alkylene or (C$_2$-C$_4$)alkenylene, n is 1, and Z represents (a) carboxy, C$_1$-C$_{10}$-alkoxycarbonyl, carbamoyl, lower alkylcarbamoyl, di-lower alkylcarbamoyl, phenyl-lower alkylcarbamoyl wherein the phenyl group is unsubstituted or monosubstituted in the same manner as indicated for the ring A, aminocarbamoyl, cyano, or 5-tetrazolyl; formyl, imino methyl which is unsubstituted or substituted by hydroxy or lower alkanoyloxy; or (c) hydroxy, lower alkoxy, C$_1$-C$_{20}$-alkanoyloxy, amino, lower alkylamino, di-lower alkylamino, lower alkanoylamino, halolower alkanoylamino, or halogen; with the provisos (a) that R$_1$ is phenyl unsubstituted or substituted as defined above, if R$_2$ represents hydrogen, Y denotes methylene and X is (alpha)—S—C(—Z)=CH—(β) wherein Z denotes carboxy or said esterified or amidated carboxy as defined above, (b) that ring A is substituted as defined above, if R$_1$ and R$_2$ both are hydrogen, Y represents oxygen or sulfur and X is (alpha)—S—C(—COOH)=CH—(β), and (c) that Y is oxygen or sulfur, if R$_1$ and R$_2$ both are hydrogen, X is (alpha)—S—C(—Z)=CH—(β) wherein Z denotes carboxy, ethoxycarbonyl, cyano, formyl or bromo, and ring A is unsubstituted or monosubstituted in 7-position by methoxy, or a tautomer, a stereoisomer or an optical isomer thereof, or a mixture of optical isomers; or a pharmaceutically acceptable salt thereof.

3. The compound of claim 1, wherein ring A is unsubstituted or monosubstituted by lower alkyl, hydroxy, lower alkoxy or halogen, R$_1$ and R$_2$, independently of one another, each represents hydrogen, lower alkyl, phenyl or hydroxy-phenyl, Y is methylene, oxygen or sulfur, X represents a bivalent radical —S—C-(—B—(Z)$_n$)=CH— the sulfur group S of which is bound directly to he alpha-position of the bicyclic ring system, B denotes a direct bond, (C$_1$-C$_4$)alkylene or (C$_2$-C$_4$)alkenylene, n is 1, and Z represents (a) carboxy, C$_1$-C$_8$-alkoxycarbonyl, carbamoyl, lower alkylcarbamoyl, phenyl-lower alkylcarbamoyl, halo-phenyl-lower alkylcarbamoyl, aminocarbamoyl, cyano, or 5-tetrazolyl; (b) formyl, imimomethyl which is substituted by hydroxy or lower alkanoyloxy; or (c) hydroxy, C$_1$-C$_{16}$-alkanoyloxy, amino or halo-lower alkanoylamino; with the provisos (a) that R$_1$ is phenyl or hydroxy-phenyl, if R$_2$ represents hydrogen, Y denotes methylene and X is (alpha)—S—C(—Z)=CH—(β) wherein Z denotes carboxy or said esterified or amidated carboxy as defined above, (b) that ring A is substituted as defined above, if R$_1$ and R$_2$ both are hydrogen, Y represents oxygen or sulfur and X is (alpha)—S—C(—COOH)=CH—(β), and (c) that Y is oxygen or sulfur, if R$_1$ and R$_2$ both are hydrogen, X is (alpha)—S—C(—Z)=CH—(β) wherein Z denotes carboxy, ethoxycarbonyl, cyano or formyl, and ring A is unsubstituted or monosubstituted in 7-position by methoxy;

or a tautomer, a stereoisomer or an optical isomer thereof, or a mixture of optical isomers; or a pharmaceutically acceptable salt thereof.

4. The compound of claim 1 wherein ring A is unsubstituted or monosubstituted by lower alkyl, lower alkoxy or halogen, R$_1$ denotes phenyl, R$_2$ represents hydrogen, Y is methylene, oxygen or sulfur, X represents a bivalent radical —S—C(—B—(Z)$_n$)=CH— the sulfur group of S which is bound directly to the alpha- or to the β-position of the bicyclic ring system, B denotes a direct bond, (C$_1$-C$_4$)alkylene or (C$_2$-C$_4$)alkenylene, n is 1, and Z represents (a) carboxy, C$_1$-C$_8$-alkoxycarbonyl, carbamoyl, lower alkylcarbamoyl, aminocarbamoyl, cyano, or 5-tetrazolyl; (b) formyl or iminomethyl which is substituted by hydroxy or lower alkanoyloxy; or (c) hydroxy, C$_1$-C$_{16}$-alkanoyloxy, or amino; or a tautomer, a stereoisomer or an optical isomer thereof, or a mixture of optical isomers; or a pharmaceutically acceptable salt thereof.

5. The compound of claim 1 wherein ring A is unsubstituted or monosubstituted by lower alkyl, lower alkoxy or halogen, R$_1$ denotes phenyl, R$_2$ represents hydrogen, Y is methylene, oxygen or sulfur, X represents a bivalent radical —S—C(—Z)=CH— the sulfur group S of which is bound directly to the alpha-position of the bicyclic ring system, Z represents carboxy, C$_1$-C$_8$-alkoxycarbonyl, carbamoyl, lower alkylcarbamoyl, cyano, 5-tetrazolyl or hydroxymethyl; or a tautomer, a stereoisomer or an optical isomer thereof, or a mixture of optical isomers; or a pharmaceutically acceptable salt thereof.

6. 4H-4-phenyl-thieno[3,2-c][1]benzopyran-2-carboxylic acid or a pharmaceutically acceptable salt thereof, according to claim 1.

7. Ethyl (4H-4-phenyl-thieno[3,2-c][1]benzopyran)-2-carboxylate according to claim 1.

8. 4H-2-carboxamido-4-phenyl-thieno[3,2-c][1]benzopyran according to claim 1.

9. N-Methyl-4H-2-carboxamido-4-phenyl-thieno[3,2-c][1]benzopyran according to claim 1.

10. A compound of formula I

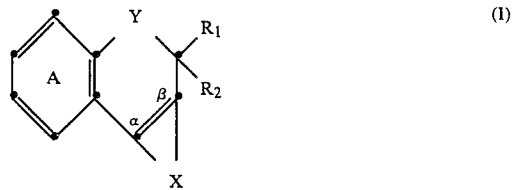

wherein ring A is unsubstituted or monosubstituted by lower alkyl, lower alkoxy or halogen, R$_1$ denotes phenyl or lower alkyl, R$_2$ represents hydrogen, Y is methylene mono or disubstituted by lower alkyl, X represents a bivalent radical —S—C(—B—(Z)$_n$)=CH— the sulfur group S of which is bonded directly to the alpha- or to the β-position of the bicyclic ring system, B denotes a direct bond, (C$_1$-C$_4$)alkylene or (C$_2$-C$_4$)alkenylene, n is 1, and Z represents (a) carboxy, C$_1$-C$_8$-alkoxycarbonyl, carbamoyl, lower alkylcarbamoyl, aminocarbamoyl, cyano, or 5-tetrazolyl; (b) formyl or iminomethyl which is substituted by hydroxy or lower alkanoyloxy; or (c) hydroxy, C$_1$-C$_{16}$-alkanoyloxy, or amino; or a tautomer, a stereisomer or an optical isomer thereof, or a mixture of optical isomers; or a pharmaceutically acceptable salt thereof.

11. 4,5-Dihydro-5-methyl-2-carboxamido-naphtho[1,2-c]thiophene.

12. Benzyl (4H-4-phenyl-thieno[3,2-c][1]benzopyran)-2-carboxylate.

13. 4Chlorobenzyl (4H-4-phenyl-thieno[3,2-c][1]benzopyran)-2-carboxylate.

14. A pharmaceutical composition for the treatment of a respiratory disease comprising a therapeutically effective amount of a compound of the formula

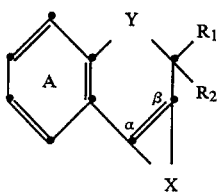

wherein ring A is unsubstituted or substituted by 1 or 2 substituents selected from the group consisting of lower alkyl, hydroxy, lower alkoxy, lower alkylenedioxy, lower alkanoyloxy, halogen, lower alkylamino, di-lower alkylamino, lower alkanoylamino, lower alkanoyl, carboxy and lower alkoxycarbonyl, $R_1$ and $R_2$, independently of one another, each represents hydrogen, lower alkyl or phenyl which is unsubstituted or substituted in the same manner as indicated above for the ring A, Y is methylene, methylene monosubstituted by lower alkyl, oxygen or sulfur, X represents a bivalent radical —S—(—B—$(Z)_n$)=CH— the sulfur group of S of which is bound directly to the alpha- or to the beta-position of the bicyclic ring system, B denotes a direct bond, lower alkylene or lower alkenylene, n is 1 or, in case B is lower alkylene or lower alkenylene, may also be 2 or 3, and Z represents carboxy, alkoxycarbonyl, carbamoyl which is unsubstituted or substituted by one or two equal or different radicals selected from the group consisting of (a) lower alkyl; (b) phenyl-lower alkyl wherein in turn the phenyl group is unsubstituted or substituted in the same manner as indicated above for the ring A; (c) amino; (d) lower alkylamino; and (e) di-lower alkylamino; esterified or amidated carboxy that can be cleaved under physiological conditions selected from lower alkanoyloxy-methoxycarbonyl, amino-lower alkanoyloxy-methoxycarbonyl, lower alkanoylamino-methoxycarbonyl, 3-phthalidyloxycarbonyl, 1-lower alkoxycarbonyloxy-lower alkoxycarbonyl, 1-lower alkoxy-lower alkoxycarbonyl, 2-oxo-1,3-dioxolen-4-yl methoxycarbonyl that is unsubstituted or substituted by lower alkyl or phenyl in the 5-position of the dioxolene ring, and carboxymethylcarbamoyl; cyano, hydroxycarbamoyl, 5-tetrazolyl, unsubstituted or lower alkyl-substituted 4,5-dihydro-2-oxoazolyl, formyl, iminomethyl which is unsubstituted or substituted by hydroxy, lower alkoxy or lower alkanoyloxy or lower alkanoyl which is unsubstituted or substituted by halogen; benzoyl or phenyl-lower alkanoyl, each unsubstituted or substituted in the phenyl ring as indicated above for the ring A; and sulfo, lower alkoxysulfonyl, sulfamoyl, lower alkylsulfamoyl, di-lower alkylsulfamoyl, hydroxy, lower alkoxy, alkanoyloxy, amino, lower alkylamino, di-lower alkylamino, lower alkyleneamino, N-morpholino, N-thiomorpholino, and N-piperazino which is unsubstituted or substituted by lower alkyl at its 4-position nitrogen atom, lower alkanoylamino, halo-lower alkanoylamino, nitro and halogen;

or a tautomer, a stereoisomer or an optical isomer thereof, or a mixture of optical isomers; or a pharmaceutically acceptable salt thereof; and a pharmaceutically acceptable carrier.

15. The composition of claim 14 wherein ring A is unsubstituted or monosubstituted by lower alkyl, hydroxy, lower alkoxy or halogen, $R_1$ and $R_2$ independently of one another, each represents hydrogen, lower alkyl, or phenyl, which phenyl is unsubstituted or monosubstituted in the same manner as indicated for the ring A, Y is methylene which is unsubstituted or mono-lower alkyl substituted, oxygen or sulfur, X represents a bivalent radical —S—C(—B—$(Z)_n$)=CH— the sulfur group S of which is bound directly to the alpha- or to the β-position of the bicyclic ring system, B denotes a direct bond, $(C_1-C_4)$alkylene or $(C_2-C_4)$alkenylene, n is 1, and Z represents (a) carboxy, $C_1-C_{10}$-alkoxycarbonyl, carbamoyl, lower alkylcarbamoyl, di-lower alkylcarbamoyl, phenyl-lower alkylcarbamoyl wherein the phenyl group is unsubstituted or monosubstituted in the same manner as indicated for the ring A, aminocarbamoyl, cyano, or 5-tetrazolyl; (b) formyl, or imino methyl which is unsubstituted or substituted by hydroxy or lower alkanoyloxy; or (c) hydroxy, lower alkoxy, $C_1-C_{20}$-alkanoyloxy, amino, lower alkylamino, di-lower alkylamino, lower alkanoylamino, halolower alkanoylamino, or halogen;

or a tautomer, a stereoisomer or an optical isomer thereof, or a mixture of optical isomers; or a pharmaceutically acceptable salt thereof; and a pharmaceutically acceptable carrier.

16. The composition of claim 14 wherein ring A is unsubstituted or monosubstituted by lower alkyl, hydroxy, lower alkoxy or halogen, $R_1$ and $R_2$, independently of one another, each represents hydrogen, lower alkyl, phenyl or hydroxy-phenyl, Y is methylene, oxygen or sulfur, X represents a bivalent radical —S—C-(—B—$(Z)_n$)=CH— the sulfur group S of which is bound directly to the alpha-position of the bicyclic ring system, B denotes a direct bond, $(C_1-C_4)$alkylene or $(C_2-C_4)$alkenylene, n is 1, and Z represents (a) carboxy, $C_1-C_8$-alkoxycarbonyl, carbamoyl, lower alkylcarbamoyl, phenyl-lower alkylcarbamoyl, halo-phenyl-lower alkylcarbamoyl, aminocarbamoyl, cyano, or 5-tetrazolyl; (b) formyl or iminomethyl which is substituted by hydroxy or lower alkanoyloxy; or (c) hydroxy, $C_1-C_{16}$-alkanoyloxy, amino or halo-lower alkanoylamino; a tautomer, a stereoisomer or an optical isomer thereof, or a mixture of the optical isomers; or a pharmaceutically acceptable salt thereof.

17. The pharmaceutical composition of claim 14 wherein the compound of formula I is ethyl (4,5-dihydro-8-fluoro-naphtho[1,2-b]thiophene)-2-carboxylate.

18. The pharmaceutical composition of claim 14 wherein the compound of formula I is 4,5-dihydro-8-fluoro-naphtho[1,2-b]thiophene-2-carboxylic acid or a pharmaceutically acceptable salt thereof.

19. The pharmaceutical composition of claim 14 wherein the compound of formula I is 4,5-dihydro-2-carboxamido-naphtho[1,2-b]thiophene.

20. The pharmaceutical composition of claim 14 wherein the compound of formula I is 4,5-dihydro-8-fluoro-2-carboxamido-naphtho[1,2-b]thiophene.

21. The pharmaceutical composition of claim 14 wherein the compound of formula I is 4,5-dihydro-5-methyl-2-carboxamido-naphtho[1,2-b]thiophene.

22. A method of treating a disease of the respiratory tract in a mammal in need thereof comprising administering to said mammal a therapeutically effective amount of a compound of formula I according to claim 19 or of a pharmaceutically acceptable salt thereof.

* * * * *